United States Patent
Berkland et al.

(10) Patent No.: US 7,651,770 B2
(45) Date of Patent: Jan. 26, 2010

(54) NANOCLUSTERS FOR DELIVERY OF THERAPEUTICS

(75) Inventors: Cory J. Berkland, Lawrence, KS (US); Lianjun Shi, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 211 days.

(21) Appl. No.: 11/610,986

(22) Filed: Dec. 14, 2006

(65) Prior Publication Data

US 2007/0172653 A1    Jul. 26, 2007

Related U.S. Application Data

(60) Provisional application No. 60/751,172, filed on Dec. 16, 2005.

(51) Int. Cl.
    *B32B 5/16*    (2006.01)
(52) U.S. Cl. .............. 428/402; 424/1.29; 424/408; 424/417; 428/403; 428/407; 436/523; 436/524; 436/528
(58) Field of Classification Search .......... 428/402, 428/403, 407; 424/1.29, 408, 417, 421; 436/523, 436/524, 528
    See application file for complete search history.

(56) References Cited

U.S. PATENT DOCUMENTS

| | | | |
|---|---|---|---|
| 5,814,370 A * | 9/1998 | Martino et al. .......... | 427/213.35 |
| 6,562,403 B2 * | 5/2003 | Klabunde et al. ........... | 427/216 |
| 6,656,568 B1 * | 12/2003 | Winningham et al. ....... | 428/145 |
| 6,669,961 B2 | 12/2003 | Kim et al. .................... | 424/489 |
| 7,060,472 B2 * | 6/2006 | Holt ............................. | 435/168 |
| 2002/0015679 A1 | 2/2002 | Kotov | |
| 2003/0138490 A1 | 7/2003 | Hu et al. ..................... | 424/486 |
| 2004/0096477 A1 | 5/2004 | Chauhan et al. | |
| 2005/0019270 A1 | 1/2005 | Finlay et al. .................. | 424/46 |
| 2005/0053667 A1 | 3/2005 | Irvine et al. ................. | 424/490 |
| 2005/0171433 A1 | 8/2005 | Boppart et al. | |
| 2005/0255164 A1 | 11/2005 | Liu et al. | |

FOREIGN PATENT DOCUMENTS

| WO | WO 03/022910 | 3/2003 |
|---|---|---|
| WO | 2003/062372 A | 7/2003 |
| WO | WO 03/100034 | 12/2003 |
| WO | 2004/096140 A | 11/2004 |

OTHER PUBLICATIONS

Adjei and Garren, "Pulmonary delivery of peptide drugs: effect of particle size on bioavailability of leuprolide acetate in healthy male volunteers," *Pharm. Res.*, 7:565-569, 1990.

(Continued)

*Primary Examiner*—H. (Holly) T Le
(74) *Attorney, Agent, or Firm*—Baker Botts L.L.P.

(57) ABSTRACT

The present invention discloses a nano-cluster that includes a plurality of nano-particles, wherein the nano-particles can disperse in response to an environmental cue. Also disclosed is a method of preventing, treating, or diagnosing a disease or condition in a subject comprising administering a therapeutically effective amount of a composition comprising nano-clusters of the present invention.

62 Claims, 9 Drawing Sheets

OTHER PUBLICATIONS

"American Lung Association State of the Air: 2006," *American Lung Association*, 2006.

Anderson, "Delivery options and devices for aerosolized therapeutics," *Chest*, 120:89S-93S, 2001.

Berkland et al., "Fabrication of PLG microspheres with precisely controlled and monodisperse size distributions," *J. Control Release*, 73:59-74, 2001.

Berkland et al., "Precise control of PLG microsphere size provides enhanced control of drug release rate," *J. Control Release*, 82:137-47, 2002.

Berkland et al., "Uniform double-walled polymer microspheres of controllable shell thickness," *J. Control Release*, 96:101-111, 2004.

Berkland et al., "Precision polymer microparticles for controlled-release drug delivery," *ACS Sym. Ser.*, 2002.

Berkland, "Control of micro- and nano-sphere size distributions: implications in drug delivery," *Chemical Engineering*, Urbana-Champaign, University of Illinois, pp. 78, 2001.

Grenha et al., "Microencapsulated chitosan nanoparticles for lung protein delivery," *Eur. J. Pharm. Sci.*, 25:427-437, 2005.

Griesenbach et al., "Advances in cystic fibrosis gene therapy," *Curr. Opin. Pulm. Med.*, 10(6):542-546, 2004.

John et al., "Discovery of potent nanoparticle P-selectin antagonist with anti-inflammatory effects in allergic airway disease," *Faseb. J.*, 17(15):2296-2298, 2003.

Johnson et al., "Delivery of albuterol and ipratropium bromide from two nebulizer systems in chronic stable asthma: efficacy and pulmonary deposition," *Chest*, 96(1):6-10, 1989.

Kim et al., "Assessment of regional deposition of inhaled particles in human lungs by serial bolus delivery method," *J. Appl. Physiol.*, 81:2203-2213, 1996.

Kumar et al., "Chitosan IFN-γ-pDNA nanoparticle (CIN) therapy for allergic asthma," *Genet. Vaccines Ther.*, 1(1):3, 2003.

Labiris and Dolovich, "Pulmonary drug delivery. Part I: physiological factors affecting therapeutic effectiveness of aerosolized medications," *Br. J. Clin. Pharmacol.*, 56:588-599, 2003.

Lindgren et al., "Clinical consequences of inadequate inhalation technique in asthma therapy," *Eur. J. Respir. Dis.*, 70:93-98, 1987.

Mainardes et al., "Microcapsules, liposomes, nanoparticles, microcells, microspheres," *J Microencapsul*, 22:13-24, 2005.

Manoharan et al., "Dense Packing and Symmetry in Small Clusters of Microspheres," *Science*, 301:483-487, 2003.

Marier et al., "Liposomal tobramycin against pulmonary infections of *Pseudomonas aeruginosa*: a pharmacokinetic and efficacy study following single and multiple intratracheal administrations in rats," *J. Antimicrob. Chemother.*, 52:247-252, 2003.

Musante et aL, "Factors affecting the deposition of inhaled porous drug particles," *J. Pharm. Sci.*, 91:1590-1600. 2002.

Newman et al., "Scintigraphic comparison of budesonide deposition from two dry powder inhalers," *Eur. Respir. J.*, 16:178-183, 2000.

Newman, "Drug Delivery to the lungs from dry powder inhalers," *Curr. Opin. Pulm. Med.*, 9:S17-S20, 2003.

Niven, "Delivery of biotherapeutics by inhalation aerosol," *Crit. Rev. Ther. Drug Carrier Syst.*, 12:151-231, 1995.

Patton and Platz, "Pulmonary delivery of peptides and proteins for systemic action," *Advanced Drug Delivery Reviews*, 8:179-196, 1992.

Patton, "Deep lung delivery of therapeutic proteins," *Chemtech*, 27:34-38, 1997.

Pritchard, "The influence of lung deposition on clinical response," *J. Aerosol Med.*, 14:S19-S26, 2001.

Rasenack and Muller, "Micron-size drug particles: common and novel micronization techniques," *Pharm. Dev. Technol.*, 9:1-13, 2004.

Reed et al., "Aerosol beclomethasone dipropionate spray compared with theophylline as primary treatment for chronic mild-to-moderate asthma," *J. Allergy Clin. Immunol.*, 101:14-23, 1998.

Schuepp et al., "Deposition of aerosols in infants and children," *J. Aerosol. Med.*, 17:153-156, 2004.

Scott et al., "Enhanced gene delivery to human airway epithelial cells using an intergrin-targeting lipoplex," *J. Gene Med.*, 3:125-134, 2001.

Sham et al., "Formulation and characterization of spray-dried powders containing nanoparticles for aerosol delivery to the lung," *Int. J. Pharm.*, 269(2):457-467, 2004.

Surendrakumar et al., "Sustained release of insulin from sodium hyaluronate based dry powder formulations after pulmonary delivery to beagle dogs," *J. Control Release*, 91:385-394, 2003.

Tsapis, "Trojan particles: large porous carriers of nanoparticles for drug delivery," *Proc. Natl. Acad. Sci. USA*, 99:12001-12005, 2002.

Wittaya-Areekul et al., "Freeze-drying of *tert*-Butanol/water cosolvent systems: a case report on formation of a friable freeze-dried powder of tobramycin sulfate," *J. Pharm. Sci.*, 91:1147-1155, 2002.

Yi et al., "Colloidal clusters of silica or polymer microspheres," *Adv. Mater.*, 16:1204-1208, 2004.

Yoshizawa et al., "Immune responsiveness to inhaled antigens: local antibody production in the respiratory tract in health and lung diseases," *Clin. Exp. Immunol.*, 100:395-400, 1995.

Jingwei Xei, et al., "Self-Assembled Biodegradable Nanoparticles Developed by Direct Dialysis for the Delivery of Paclitaxel", Pharmaceutical Research, vol. 22, No. 12, 2005, pp. 2079-2089.

* cited by examiner

- Therapeutic nanoparticle
- Responsive polymer

Nanoparticles organized into clusters

Tunable diameter

Deposition triggers dispersion of nanoparticles

NANOCLUSTERS FOR DELIVERY OF THERAPEUTICS

CROSS-REFERENCE TO RELATED APPLICATIONS

This application claims the benefit of U.S. Provisional Application No. 60/751,172, filed Dec. 16, 2005, the contents of which are incorporated by reference.

BACKGROUND OF THE INVENTION

A. Field of the Invention

The present invention relates generally to delivery vehicles that can be used to transport active ingredients to a subject. In certain aspects, the delivery vehicles can be nano-clusters that can be used in preventative or therapeutic applications.

B. Background of the Invention

Millions of people worldwide suffer from a wide variety of diseases or conditions that would benefit from the effective delivery of therapeutic and or preventative agents. Examples of these diseases or conditions include pulmonary diseases, circulatory diseases, muscular diseases, bone diseases, cancers, etc.

The use of nano-particles as drug delivery vehicles has been employed for a variety of indications (John 2003). Nano-particles, for example, have been shown to improve the dissolution of poorly water-soluble drugs and enhance the transport of drugs both intra- and paracellularly. In addition, literature indicates that plasmid DNA can be effectively delivered by polycantionic polymers that form nano-particles when mixed with DNA resulting in enhanced gene expression (Kumar 2003). Research efforts on nano-particle-mediated gene therapy also address treating genetic disorders such as Cystic Fibrosis (Griesenbach 2004).

Most nano-particle formulations are designed for action at the cellular level. This assumes the efficient delivery of the nano-particle to the appropriate cellular target. However, current nano-particle treatment options are limited in the ability to access the cellular target. For example, two research groups are currently investigating microencapsulated nano-particles as a mode of nano-particle delivery to the pulmonary epithelium (Sham 2004, Grenha 2005). These efforts are hindered by the common inability to control microparticle size, distribution, and difficulty in delivering a large payload of therapeutic nano-particles.

SUMMARY OF THE INVENTION

The present invention overcomes the deficiencies in the art by providing effective drug delivery systems that can: (1) formulate nano-particles as a nano-cluster to facilitate handling, administering, or targeting, for example; and (2) maintain the cluster or disperse the nano-particles at the targeted site.

In one aspect of the present invention, there is disclosed a nano-cluster comprising a plurality of nano-particles. In certain non-limiting aspects, the nano-cluster is maintained at the targeted site (e.g., the nano-cluster does not disperse into separate nano-particles). In other aspects, the nano-particles disperse in response to an environmental cue. The nano-cluster, in certain non-limiting embodiments, can have a size of about 1 to about 200 microns. In certain aspects, the nano-cluster size is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 160, 170, 180, 190, or 200 microns. In other aspects, the size of the nano-cluster can be greater than 200 microns (e.g., 210, 220, 230, 240, 250, 300, 350, 400, 450, 500, 600, 700, or more microns in size.) The nano-cluster of the present invention can also have a variety of shapes (e.g, spherical and non-spherical shapes). In certain embodiments, the nano-cluster can be solid or hollow. A person of ordinary skill in the art will recognize that a solid nano-cluster can be completely solid throughout or can have spaces, such as pores or a hollow core, that are created by the packing of the nano-particles within the nano-cluster. The size of these packing spaces can be from about 1 nm to about 1000 nm, in non-limiting aspects. In certain aspects, the size of the packing spaces can be about 1, 2, 3, 4, 5, 6, 7, 8, 9, 10, 20, 30, 40, 50, 60, 70, 80 , 90, 100, 150, 200, 250, 300, 350, 400, 450, 500, 550, 600, 650, 700, 750, 800, 850, 900, 950, 1000 or more nanometers, in non-limiting aspects. Hollow nano-clusters can have an empty space or cavity. The size of the cavity can vary, for example, from about 50 m to about 20 µm, in non limiting aspects. The size of the cavity, for example, can be 50, 100, 150, 200, 250, 300, 3500, 400, 450, 500, 550, 600, 650, 700, 750, 800 . . . 20 µm, and any range derivable therein.

The nano-particles that are included in the nano-cluster, in some embodiments, are not held (e.g., adhered or chemically bound (e.g., covalent bond, non-covalent bond, van der waals forces)) together by a functional group on the nano-particles. The nano-particles can be in direct contact with one another in some aspects. In other aspects, the nano-particles are not in direct contact with one another. In certain embodiments of the present invention, the nano-particles are not encapsulated. In other embodiments, the nano-particles do not include a functional group. In other aspects, however, the nano-particles can include a functional group such as, for example, a carboxyl, sulhydryl, hydroxyl, or amino group. All types of functional groups that can be used to bind other nano-particles together, active ingredients to the surface of nano-particles, or other compounds are contemplated as being useful with the present invention.

In certain embodiments, the nano-cluster can include an active ingredient. Non-limiting examples of active ingredients that are contemplated as being useful in the context of the present invention include those known to a person of ordinary skill and those described throughout this specification. By way of example only, active ingredients can include medical pharmaceuticals and specialties such as preventive agents, for example vaccines, diagnostic agents, for example tracers of various types and imaging enhancers, therapeutic agents, for example small molecules (e.g., nucleic acids, proteins, peptides, polypeptides, etc.), drugs, peptides, and radiation, immuno-modulators, vaccine and virus vectors, and combinations of these classes. The nano-particles can include particular embodiments, respirable non-medical specialties such as physiochemical agents, for example gas antidotes, biophysical modulators, for example paramagnetics, emitters, for example electromagnetic wave emitters, and imaging enhancers. The active ingredients, in certain embodiments, can be associated with the nano-particles. For example, the active ingredients can be entangled, embedded, incorporated, encapsulated, bound to the surface (e.g., covalently or non-covalently bonded), or otherwise associated with the nano-particle. In certain preferred aspects, the active ingredient is the nano-particle. In other aspects, the nano-particles can include a polymer material (including, for example, biodegradable and non-biodegradable polymers). Non-limiting examples of polymer materials that can be used include those known to a person of ordinary skill and those described throughout this specification. In certain embodiments, the nano-particles can include a mixture of a polymer and an active ingredient.

In other non-limiting embodiments, the nano-cluster or nano-particles, or both, can include at least one, two, three, four, five, six, seven, or more different active ingredients. In a preferred embodiment, the nano-cluster or nano-particles include a first drug on its surface, and a second active ingredient encapsulated within the nano-cluster or nano-particles or other incorporated into the nano-cluster or nano-particle material. It is contemplated that a nano-cluster can release the active ingredients in a given environment, or after a given period of time in a controlled manner. For example, a nano-cluster having at least one active ingredient can be released in response to an environmental cue or after a pre-determined amount of time. Also by way of example only, a nano-cluster having at least two different active ingredients can be released in response to different environmental cues or after pre-determined periods of time. For example, active ingredient 1 can be released first and then active ingredient 2 can be released second. In certain non-limiting aspects, the release of the first active ingredient can improve the performance of the second active ingredient.

In other particular aspects, the nano-clusters of the present invention can include a dispersing material that holds the plurality of nano-particles together and/or disperses the nano-particles in response to an environmental cue. The dispersing materials that can be used with the present invention include those materials that are known to a person of skill in the art and those that are disclosed throughout this specification. Non-limiting examples of dispersing material include liquid sensitive materials (e.g., water-soluble materials (e.g., polymers)), biodegradable polymers, polyelectrolytes, metals, surfactants, polymeric cross-linkers, small molecule cross-linkers, pH sensitive materials, pressure sensitive materials, enzymatic sensitive materials, and temperature sensitive materials. Non-limiting examples of environmental cues that can be used with the present invention include liquid (e.g., water, blood, mucous, solvent, etc.), a selected pH range, a selected temperature range, an electric current, a selected ionic strength, pressure, the presence of a selected enzyme, protein, chemical, electromagnetic wavelength range (e.g., visible light, UV light, infrared, ultraviolet light, microwaves, X-rays, and gamma-rays), or the presence of an external force (e.g., vibration, shearing, shaking, etc.). In certain aspects, the dispersing material can be coated onto the surface of the nano-particles before or after nano-cluster formation. In certain embodiments, the dispersing material can be between the nano-particles or link the nano-particles together (e.g., covalently or non-covalently couple a first nano-particle to a second nano-particle). The dispersing material can be adhered to or covalently or non-covalently coupled to the nano-particles.

In particular embodiments of the present invention, the nano-cluster can include from about 1% to about 99% by weight or volume of the nano-particles or dispersing materials. The nano-cluster can also be completely made up of nano-particles (i.e., 100%). In preferred embodiments, the nano-cluster includes from about 10% to about 90%, 15% to about 80%, 20% to about 70%, 30% to about 60%, and about 40% to about 50% of nano-particles or dispersing materials. In certain embodiments, the nano-cluster includes at least 50% of the nano-particles or dispersing material.

Another embodiment to the present invention is a composition comprising a nano-cluster of the present invention. The composition in certain non-limiting aspects can have a plurality (e.g., at least 2, 3, 4, 5, 6, 7, 8, 9, 10, 20, 30, 40, 50, 60, 70, 80, 90, 100, 200, 300, 400, 500, or more nano-clusters. The composition can further include an active ingredient. As discussed throughout this specification, the composition can be formulated into a dry powder, an aerosol, a spray, a tablet, or a liquid. The compositions of the present invention can include at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of the nano-clusters of the present invention. In certain aspects, the compositions of the present invention can include a plurality of identical or similar nano-clusters. In other aspects, the compositions of the present invention can include at least 2, 3, 4, 5, 6, 7, 8, 9, 10, or more nano-clusters that have different characteristics (e.g., different active ingredients attached, different shapes, hollow or solid, etc.). The compositions of the present invention can be formulated into a pharmaceutically acceptable carrier.

In another embodiment, there is disclosed a method of preventing or treating a disease or condition in a subject comprising administering a therapeutically effective amount of a composition comprising a nano-cluster of the present invention to a subject (e.g., human, pigs, horses, cows, dogs, cats, mouse, rat, rabbit, or any other mammal and non-mammals) in need of the composition. The method can further include a method for determining whether a subject is in need of the prevention or treatment. The disease or condition can include all types of diseases or conditions known to a person of skill in the art and discussed throughout this specification. In certain preferred aspects, the disease or condition can be a pulmonary associated disease or condition (e.g., common cold, flu, cystic fibrosis, emphysema, asthma, tuberculosis, severe acute respiratory syndrome, pneumonia, lung cancer, etc.), a circulatory disease or condition, a muscular disease or condition, a bone disease or condition, an infection, a cancer, etc. In certain embodiments, the method can include the administration of a second therapy used to treat or prevent the disease (e.g., combination therapy). In preferred embodiments, the compositions of the present invention are administered nasally. Other modes of administration known to those of skill in the art or discussed in this specification are also contemplated. In particular aspects, the nano-clusters within the composition are delivered to the deep lung (e.g., bronchiole or alveolar regions of the lung).

In certain preferred aspects of the present invention, the nano-clusters of the present invention can be used to deliver vaccines or components of vaccines. For instance, cells of the immune system, especially macrophages and dendrocytes, are targets for immunization. These "professional" antigen-presenting cells (APCs) can elicit a desired T-cell response to vaccine components. APCs are typically capable of phagocytosis of particles in the range of 1 to 10 μm. By generating in this size range nano-clusters or nano-particles containing vaccine components, one can passively target delivery of the vaccine to APCs. U.S. Pat. No. 6,669,961, for example, provides a non-limiting explanation of this process.

The nano-clusters of the present invention can also have a particular mass density. In certain preferred embodiments, for example, the mass density can be greater than, equal to, or less than 0.1 g/cm$^3$. In particular embodiments, the mass density of the nano-clusters of the present invention can be about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 g/cm$^3$, or greater.

Also disclosed is a method of preparing a nano-cluster comprising: (i) obtaining a plurality of nano-particles; (ii) obtaining a dispersion material (when desired); and (iii) admixing (i) and (ii), wherein the admixture is formulated into a nano-cluster. In certain aspects, obtaining a plurality of nano-particles comprises: (i) obtaining an aqueous suspension of nano-particles; (ii) emulsifying the suspension into a non-aqueous phase; (iii) allowing water in the aqueous suspension to absorb into the non-aqueous phase; (iv) allowing the nano-particles to aggregate together; and (v) retrieving the aggregated nano-particles. In other non-limiting embodiments, obtaining a plurality of nano-particles includes: (i) obtaining a non-aqueous suspension of nano-particles; (ii) emulsifying the suspension into an aqueous phase; (iii) allowing liquid in the non-aqueous suspension to absorb into the aqueous phase; (iv) allowing the nano-particles to aggregate together; and (v) retrieving the aggregated nano particles. The disclosed method represents a non-limiting method with other methods being evident by one skilled in the art (e.g. emulsion/solvent evaporation, extraction, spray-drying, spray freeze-drying, self-assembly in solution, etc.). In certain aspects, it is contemplated that the nano-clusters can be prepared in a solution without using spray and/or freeze dry techniques. It is also contemplated that the nano-clusters can be recovered from the solution by using freeze dry or spray dry techniques that are known to those of skill in the art. As noted throughout this specification, the nano-cluster can be included within a composition. The composition can be formulated into a liquid, a spray, an aerosol, or a dry powder in non-limiting embodiments.

Also disclosed is a method of delivering an active ingredient to a subject in need comprising obtaining composition comprising a nano-cluster of the present invention and an active ingredient and administering the composition to the subject. In non-limiting aspects, the active ingredient is encapsulated in the nano-particle, incorporated within the nano-particle material, conjugated to the nano-particle, absorbed or coupled to the nano-particle.

In yet another embodiment of the present invention, there is disclosed a method of preparing a nano-cluster comprising: (i) obtaining a first nano-particle and a second nano-particle; and (ii) admixing the first and second nano-particles, wherein the nano-particles self assemble to form a nano-cluster. The first and second nano-particles, for example, can have hydrophobic properties, hydrophilic properties, or a mixture of both. In other aspects, the first or second nano-particles can have an electrostatic charge. For example, the first nano-particle can be positively charged and the second nano-particle negatively charged, and vice versa. The self-assembly, in particular embodiments can be based on an electrostatic interaction between the first and second nano-particles. In other non-limiting aspects, the self-assembly can be based on a hydrophobic or hydrophilic interaction between the first and second nano-particles. The first and second nano-particles can self assemble in solution to form the nano-cluster in certain embodiments. In particular aspects, preparation of the nano-clusters does not require the use of spray and/or freeze dry techniques; rather nano-cluster formation can occur in solution. The nano-clusters can be recovered from the solution by using freeze dry or spray dry techniques that are known to those of skill in the art. In other aspects, the method of preparing the nano-cluster can further comprise obtaining a dispersion material and admixing the dispersion material with the first and second nano-particles.

As disclosed is a method of storing nano-particles comprising forming the nano-particles into a nano-cluster. The nano-particles, for instance, can be stored as a liquid, a spray, and aerosol, or a dry powder. The method of storing the nano-particles can further comprise returning the nano-cluster to nano-particles. In certain aspects, returning the nano-cluster to nano-particles can include subjecting the nano-cluster to an environmental cue. As noted above and throughout this specification, non-limiting examples of environmental cues include water, a selected pH, a selected temperature, a selected enzyme, a selected chemical, a selected electromagnetic wavelength range, vibration, or shearing. In certain particular aspects, the nano-cluster can include a dispersing material that holds the nano-particles together and/or disperses the nano-particles in response to an environmental cue. Non-limiting examples of dispersing materials include a water soluble polymer, a biodegradable polymer, a polyelectrolyte, a metal, a polymeric cross-linker, a small molecule cross-linker, a pH sensitive material, a surfactant, or a temperature sensitive material.

It is contemplated that any embodiment discussed in this specification can be implemented with respect to any method or composition of the invention, and vice versa. Furthermore, compositions of the invention can be used to achieve methods of the invention.

The terms "inhibiting," "reducing," "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The term "about" or "approximately" are defined as being close to as understood by one of ordinary skill in the art. In one non-limiting embodiment the terms are defined to be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1. Therapeutic nano-particles are organized into a nano-cluster having a defined (and tunable) diameter. Upon contact with an environmental cue, the dispersive material triggers dispersion of the nano-particles.

FIG. 2. Electron micrographs of (A) ~100 nm silica particles that compose the (B) ~6 μm nano-cluster. (C) Represents typical nano-cluster distribution. Scale bar in (C) represents 10 μm.

FIG. 3. Nano-clusters can be fabricated with a broad or narrow size distribution (left top and bottom). Adjusting fabrication conditions and/or dispersing material used allows for the formation of a solid (top right) or hollow (bottom right) clusters.

FIG. 4. Uniform (~75 μm) nano-clusters composed of polystyrene nano-particles.

FIG. 5. Electron micrographs of (A) 225 nm silica nanoparticles coated with a dispersion material (light gray corona) and (B) a 9 μm nano-cluster of the silica nano-particles coated with dispersion material.

FIG. 6. The dispersion of nano-clusters over time composed of nano-particles coated with a hydrolysable polymer was a function of pH as determined by (A) absorption of light at 480 nm and (B) visual inspection. (C) Size analysis of the dispersion shows polydisperse agglomerates are liberated from the nano-clusters, which then break down into monodisperse nano-particles.

FIG. 7A, FIG. 7B, FIG. 7C. The (FIG. 7A) geometric and (FIG. 7B) aerodynamic size distributions of PLGA nanoclusters produced by increasing the concentration of nanoparticles (black=0.68 mg/ml, red=1.36 mg/ml, green=2.16 mg/ml, blue=2.72 mg/ml). FIG. 7C Scanning electron micrograph of nanocluster structure. Scale bar=5 μm.

FIG. 8A, FIG. 8B, FIG. 8C, FIG. 8D, FIG. 8E, FIG. 8F. Laser scanning confocal micrographs of PLGA nanoparticle nanoclusters. FITC-labeled PVAm-coated nanoparticles (FIG. 8A and FIG. 8D) and rhodamine-labeled PEMA-coated nanoparticles (FIG. 8B and FIG. 8E) are both identified within the nanocluster structure. FIG. 8C and FIG. 8F Overlays of the micrographs reveal the diffuse structure of the nanoclusters. Scale bar=5 μm.

FIG. 9. Scanning electron microscope (SEM) image of a population of nifedipine nanoparticles.

FIG. 10. SEM image of nifedipine nanoparticle clusters.

FIG. 11. Illustration of the geometric diameter of the nanoclusters comprising DOTAP/PLGA nanoparticles and ovalbumin.

FIG. 12. SEM images of the nanoclusters comprising DOTAP/PLGA nanoparticles and ovalbumin.

DESCRIPTION OF ILLUSTRATIVE EMBODIMENTS

Current drug delivery treatment options can often be ineffective due to inefficient delivery of an active ingredient to a targeted site. Many of the current drug delivery systems are limited in their ability or efficiency to access a specifically targeted site. Although nano-particles offer several advantages for delivering drugs (e.g. improved dissolution of low solubility API, intracellular and transcellular transport, etc.), the use of nano-particles, for example, can be hindered by the inability to deliver nano-particles to the site of drug action (e.g. dried nano-particles are too small to deposit efficiently in the lungs, can avoid detection by APCs, etc.). In addition, nano-particles are often difficult to handle at an industrial scale and a controlled clustering process may ease handling and allow facile reconstitution and formulation of nano-particles or nano-clusters for delivering drugs.

The nano-clusters of the present invention can be used to deliver active ingredients to a targeted site. The size and distribution of the disclosed nano-clusters and nano-particles can be designed for a desired route of administration and/or for the treatment of a particular disease or condition. In one aspect, for example, the nano-clusters provide an effective and efficient drug delivery system that can carry nano-particles to a targeted site via the nano-cluster. In certain aspects, the nano-cluster is maintained at the targeted site. In other aspects, the nano-cluster can disperse the nano-particles at the targeted site. Additionally, the nano-clusters can be formulated with the appropriate physicochemical properties to carry and controllably release therapeutic nano-particles or active ingredients to a targeted site.

Another aspect of the invention is that the nano-clusters can be prepared in a solution without using standard spray and/or freeze dry techniques known to those of ordinary skill in the art.

These and other aspects of the present invention are described in further detail in the following sections.

A. Nano-Clusters

In certain non-limiting aspects, a nano-cluster of the present invention can include a plurality of nano-particles with or without a dispersing material that holds the plurality of nano-particles together. The dispersing material can also be used to disperse the nano-particles in response to an environmental cue. An active ingredient can also be incorporated into the nano-cluster. In other aspects, the nano-particle can be the active ingredient. FIG. 1, for example, illustrates a nano-cluster having a therapeutic nanoparticle and a dispersing material. This delivery system provides the advantage of particle clusters appropriately sized for delivery (e.g., lung, nasal passage, M-cells in the digestive tract, uptake by antigen presenting cells, etc.) with the benefits of nano-particles, such as improvements in drug solubility, bioavailability, transport through biological barriers, intracellular delivery, etc. As described in more detail throughout this specification, changing the nature of the dispersing material allows for the development of an environmentally responsive nano-particle delivery system and/or biosensors. In addition, the special arrangement of nano-particles within the cluster can allow discrete control over the duration and concentration of an active ingredient, a concept that can also be facilitated by the independent formulation of each nano-particle type before cluster formation.

The inventors have successfully formulated nanoclusters from a variety of nanoparticulate materials and have controlled the dispersion of clusters into constituent nanoparticles in aqueous solution (see Examples 1-3 below). In a non-limiting aspect, the inventors obtained a colloidal suspension of nanoparticles in deionized water which is subsequently emulsified into octanol. Water in the dispersed droplets then absorbs into the octanol phase. Nanoparticles can pack together as water is extracted from individual droplets until an aggregate of nanoparticles remains (FIG. 2). The size of the droplet, in certain non-limiting embodiments, can serve as a template for controlling the size of the resulting nano-clusters depending on the concentration of nanoparticles within the droplet. In other aspects, the clustered nanoparticles in FIG. 2 can be held together by hydrophobic, coulombic, and/or Van der Waals forces and can resist dispersion into aqueous media.

These and other aspects of the nano-clusters of the present invention are described in further detail in the following subsections.

Figure 3:
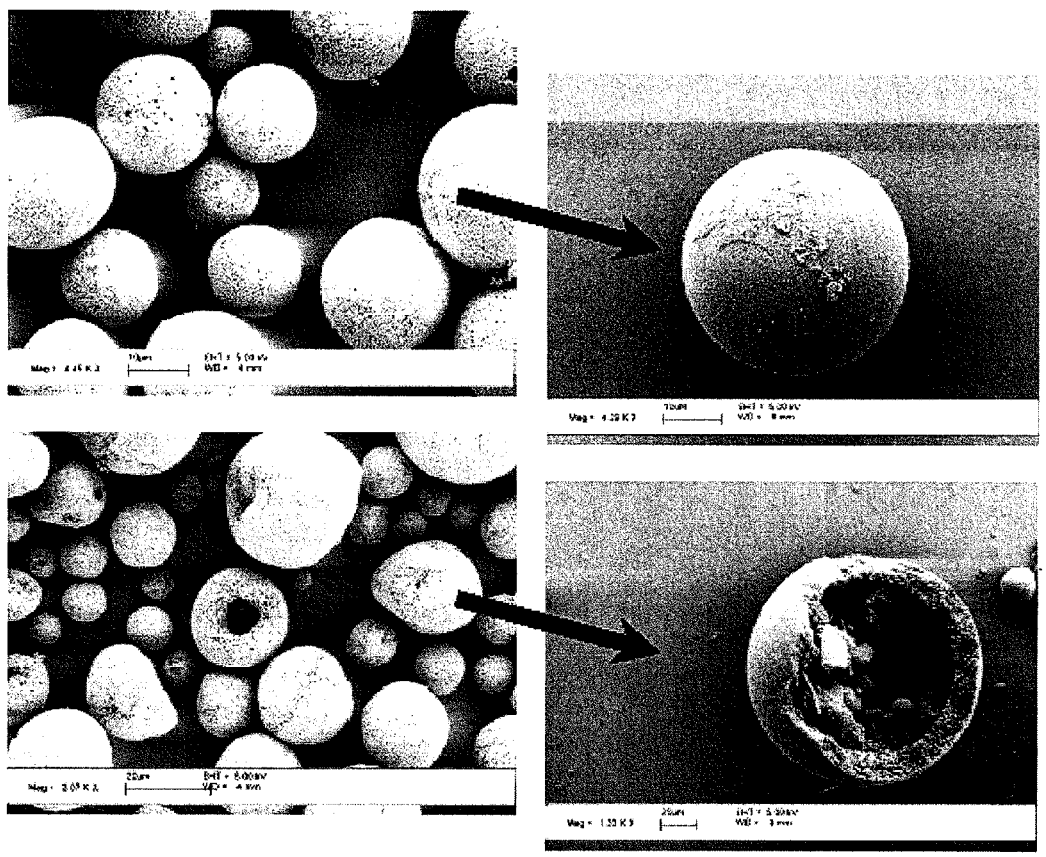

The term "nano-cluster," as that term is used in the specification and/or claims, means a cluster of nano-particles arranged such that the surface of the nano-particles are in contact with one another as shown in FIG. 2.

1. Nano-Particles

A nano-particle is a microscopic particle whose size is measured in nanometers. In preferred embodiments, the nanoparticles of the present invention have a size of from about 1 to about 3000 nanometers. In more particular aspects, the nano-particle has a size of 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, or more nanometers, or any range derivable therein.

It is contemplated that all types of materials and structures, including inorganic and organic materials, can be used for the nano-particles of the present invention. Non-limiting examples of these materials and structures include active ingredients (see specification), polymersomes, liposomes, and polyplexes. Additional non-limiting materials include poly(orthoesters), poly(anhydrides), poly(phosphoesters), poly(phosphazenes) and others. In preferred aspects, the material is the biodegradable polymer poly(lactic-co-glycolic acid) (PLGA). PLGA is a well-studied polymer for drug delivery and is FDA-approved for a number of in vivo applications. Other non-limiting materials include, for example, polyesters (such as poly(lactic acid), poly(L-lysine), poly (glycolic acid) and poly(lactic-co-glycolic acid)), poly(lactic acid-co-lysine), poly(lactic acid-graft-lysine), polyanhydrides (such as poly(fatty acid dimer), poly(fumaric acid), poly(sebacic acid), poly(carboxyphenoxy propane), poly (carboxyphenoxy hexane), copolymers of these monomers and the like), poly(anhydride-co-imides), poly(amides), poly (ortho esters), poly(iminocarbonates), poly(urethanes), poly (organophosphazenes), poly(phosphates), poly(ethylene vinyl acetate) and other acyl substituted cellulose acetates and derivatives thereof, poly(caprolactone), poly(carbonates), poly(amino acids), poly(acrylates), polyacetals, poly(cyanoacrylates), poly(styrenes), poly(vinyl chloride), poly(vinyl fluoride), poly(vinyl imidazole), chlorosulfonated polyolefins, polyethylene oxide, copolymers, polystyrene, and blends or co-polymers thereof. In certain preferred aspects, the nano-particles include hydroxypropyl cellulose (HPC), N-isopropylacrylamide (NIPA), polyethylene glycol, polyvinyl alcohol (PVA), polyethylenimine, chitosan, chitin, dextran sulfate, heparin, chondroitin sulfate, gelatin, etc. and their derivatives, co-polymers, and mixtures thereof. A non-limiting method for making nano-particles is described in U.S. Publication 2003/0138490, which is incorporated by reference.

In certain embodiments, the nano-particles can be associated with an active ingredient (e.g., entangled, embedded, incorporated, encapsulated, bound to the surface, or otherwise associated with the nano-particle). In certain preferred aspects, the active ingredient is the nano-particle. In a preferred but non-limiting aspect, the active ingredient is a drug such as a pure drug (e.g., drugs processed by crystallization or supercritical fluids, an encapsulated drug (e.g., polymers), a surface associated drug (e.g., drugs that are absorbed or bound to the nano-particle surface), a complexed drugs (e.g., drugs that are associated with the material used to form the nano-particle).

The nano-particles of the present invention, in certain embodiments, do not include a functional group. In other aspects, however, the nano-particles can include a functional group such as, for example, a carboxyl, sulhydryl, hydroxyl, or amino group. All types of functional groups that can be used to bind other nano-particles together, active ingredients to the surface of nano-particles, or other compounds are contemplated as being useful with the present invention. For instance, the functional groups can be available for drug binding (covalent or electrostatic).

2. Dispersing Material

In certain aspects of the present invention, the dispersing material can serve several functions. For example, it can be used to hold (e.g., adhere or chemical bind (e.g., covalent bond, no-covalent bond, van der wall forces) the nano-particles to one another via the dispersing material. In other aspects, the dispersing material can disperse the nano-particles at a targeted site in response to an environmental cue. This dispersing can occur, for example, when the dispersing material breaks-down, disintegrates, or other changes in such a way that it is no longer capable of holding the nano-particles together.

Non-limiting examples of dispersing materials that are contemplated as being useful with the present invention include liquid sensitive materials (e.g., water-soluble materials) such as polyoxyethylene sorbitan fatty acid esters, polyglycerol fatty acid esters, polyoxyethylene deriviatives, and analogues thereof, sugar esters, sugar ethers, sucroglycerides, (e.g. sucrose, xylitol and sorbitol) etc., biodegradable polymers (see list of polymers for nano-particle preparation), polyelectrolytes such as dextran sulfate, polyethylenimine, chitosan, chondroitin sulfate, heparin, heparin sulfate, poly (L-lysine), etc., metals (calcium, zinc, etc.), polymeric cross-linkers (polymethacrylate or similar derivatives with this functionality, poly(glutamic acid), poly(phosphorothioates), poly(propylene fumarate)-diacrylate, etc. and/or polymers with appropriate terminal or side chain reactive groups, small molecule cross-linkers (di-expoxies, di-acids, di-amines, etc.) such as 2-methylene-1,3-dioxepane, gluteraldehyde, dithiobis succinimidyl propionate, pH sensitive materials such as poly(γ-glutamic acid), enzymatic sensitive materials such as poly(amino acids) (peptides, proteins, etc.) like poly (N-substituted alpha/beta-asparagine)s, polysaccharides, lipids, oils, etc., and temperature sensitive material such as (2-hydroxyethyl methacrylate), poly(N-isopropylacrylamide), poly(2-ethylacrylic acid-co-N-[4-(phenylazo)phenyl] methacrylamide), polymers of acrylic acid or acrylamide and related polymers including and co-polymers or blends of these in addition to those previously mentioned as nano-particle forming materials, and surfactants (e.g., nonionic, cationic, anionic, cryptoanionic, and zwitterionic surfactants (See McCutcheon's Emulsifiers & Detergents (2001); U.S. Pat. Nos. 5,011,681; 4,421,769; 3,755,560, 6,117,915)). Non-limiting examples of surfactants include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, cetyl phosphate, potassium cetyl phosphate, diethanolamine cetyl phosphate, polysorbate 20, polysorbate 60, polysorbate 80, glyceryl stearate, PEG-100 stearate, tyloxapol, cetyltrimethylammonium bromide (CTAB), pluronic-68, and mixtures thereof.

Non-limiting examples of environmental cues that can cause the dispersing material to no longer be capable of holding the nano-particles together include liquid (e.g., water, blood, mucous, solvent, etc.), a selected pH range, a selected temperature range, an electric current, a selected ionic strength, pressure, the presence of a selected enzyme, protein, DNA, chemical, electromagnetic wavelength range (e.g., visible light, UV light, infrared, ultraviolet light, microwaves, X-rays, and gamma-rays), or the presence of an external force (e.g., vibration, shearing, shaking, etc.).

3. Active Ingredients

In certain non-limiting aspects, the nano-clusters of the present invention can include an active ingredient. Active ingredients include, but are not limited to, any component, compound, or small molecule that can be used to bring about a desired effect. Non-limiting examples of desired effects of the present invention include diagnostic and therapeutic effects. For example, a desired effect can include the diagnosis, cure, mitigation, treatment, or prevention of a disease or condition. An active ingredient can also affect the structure or function of body part or organ in a subject.

Active ingredients which can be used by the present invention include but are not limited to nucleic acids, proteins and peptides, hormones and steroids, chemotherapeutics, NSAIDs, vaccine components, analgesics, antibiotics, anti-depressants, etc. Non-limiting examples of nucleic acids that can be used include DNA, cDNA, RNA, iRNA, siRNA, anti-sense nucleic acid, peptide-nucleic acids, oligonucleotides, or nucleic acids that are modified to improve stability (e.g., phosphorothioates, aminophosphonates or methylphosphonates).

Proteins and peptides that can be used with the present invention include but are not limited to human growth hormone, bovine growth hormone, vascular endothelial growth factor, fibroblast growth factors, bone morphogenic protein, tumor necrosis factors, erythropoietin, thrombopoietin, tissue plasminogen activator and derivatives, insulin, monoclonal antibodies (e.g., anti-human epidermal growth factor receptor2 (Herceptin), anti-CD20 (Rituximab), anti-CD 18, anti-vascular endothelial growth factor, anti-IgE, anti-CD 11a) and their derivatives, single-chain antibody fragments, human deoxyribonuclease I (domase alfa, Pulmozyme), type-1 interferon, granulocyte colony-stimulating factor, leuteinizing hormone releasing hormone inhibitor peptides, leuprolide acetate, endostatin, angiostatin, porcine factor VIII clotting factor, interferon alfacon-1, pancrelipase (pancreatic enzymes), ovalbumin, nifedipine, loratadine, etc.

Non-limiting examples of hormones and steroids (e.g., corticosteroids) that can be used include norethindrone acetate, ethinyl estradiol, progesterone, estrogen, testosterone, prednisone and the like.

Chemotherapeutics that can be used include but are not limited to taxol (Paclitaxel), vinblastine, cisplatin, carboplatin, tamoxifen and the like.

Non-limiting examples of NSAIDs include piroxicam, aspirin, salsalate (Amigesic), diflunisal (Dolobid), ibuprofen (Motrin), ketoprofen (Orudis), nabumetone (Relafen), piroxicam (Feldene), naproxen (Aleve, Naprosyn), diclofenac (Voltaren), indomethacin (Indocin), sulindac (Clinoril), tolmetin (Tolectin), etodolac (Lodine), ketorolac (Toradol), oxaprozin (Daypro), and celecoxib (Celebrex).

Vaccine components that can be used include but are not limited to Hepatitis B, polio, measles, mumps, rubella, HIV, hepatitis A (e.g., Havrix), tuberculosis, etc.

Non-limiting examples of analgesics include but are not limited to aspirin, acetaminophen, ibuprofen, naproxen sodium and the like.

Antibiotics include but are not limited to amoxicillin, penicillin, sulfa drugs, erythromycin, streptomycin, tetracycline, clarithromycin, tobramycin, ciprofloxacin, terconazole, azithromycin and the like.

Anti-depressants include but are not limited to Zoloft, fluoxetine (Prozac), paroxetine (Paxil), citalopram, venlafaxine, fluvoxamine maleate, imipramine hydrochloride, lithium, nefazodone and the like.

Other active ingredient that can be used with the present invention include but are not limited to sildenafil (Viagra), acyclovir, gancyclovir, fexofenidine, celecoxib (Celebrex), rofecoxib, androstenedione, chloroquine, diphenhydramine HCl, buspirone, doxazocin mesylate, loratadine, clomiphine, zinc gluconate, zinc acetate, hydrocortisone, warfarin, indinavir sulfate, lidocaine, novacaine, estradiol, norethindrone acetate, medroxyprogesterone, dexfenfluramine, dextroamphetamine, doxycycline, thalidomide, fluticasone, fludarabine phosphate, etanercept, metformin hydrochloride, hyaluronate, tetrazocin hydrochloride, loperamide, ibogaine, clonazepam, ketamine, lamivudine (3TC), isotretinoin, nicotine, mefloquine, levofloxacin, atorvastatin (Lipitor), miconazole nitrate (Monistat), ritonavir, famotidine, simvastatin (Zocor), sibutramine HCl monohydrate, ofloxacin, lansoprozole, raloxifene (Evista), zanamivir (Relenza), oseltamivir phosphate, 4-phenylbutyric acid sodium salt, chlorpromazine, nevirapine, zidovudine, and cetirizine hydrochloride (Zyrtec).

Non-limiting examples of additional active ingredients can be found in Physician's Desk Reference 2000, 54th Edition, ISBN: 1563633302, AHFS 99 Drug Information, Amer. Soc. of Health System, ISBN: 1879907917 and U.S. Pat. No. 5,019,400, all of which are incorporated by reference.

B. Nano-Cluster Formulation Variables and Tunability

Figure 4:
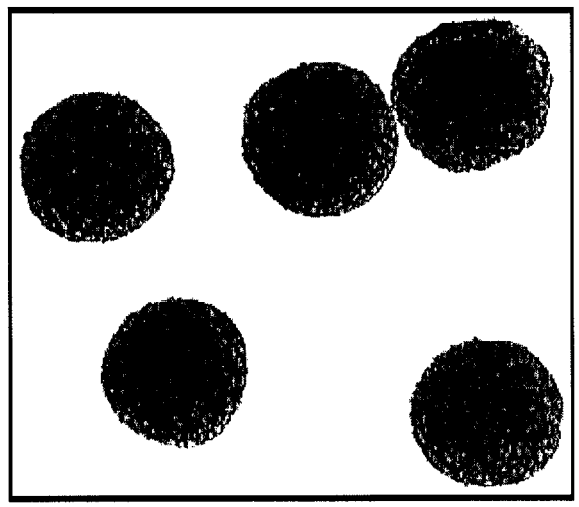

Varying nanoparticle type or size, dispersion properties, dispersing materials, and processing conditions, for example, can be used to tune the nano-cluster to a targeted size, density, and/or dispersability. For example, FIGS. 3 and 4 illustrate that varying processing conditions can be used to create nano-clusters with a broad or narrow size range and also allows for the formation of solid or hollow nano-clusters. Controlling the droplet size in an emulsion or sprayed from a nozzle can facilitate the formation of uniform nano-clusters. Varying the solvent and extraction phase, temperature, humidity, etc. as well as the properties of the nano-particles can control the morphology of the nano-cluster. For example, rapid extraction of the nanoparticle-carrying solution may result in a core/shell structure while slow remove of this phase allows time for nano-particles to diffuse from the interface and form a more dense nano-cluster structure. In another example, controlling nanoparticle physicochemical properties can provide a driving force for the nanoparticle towards or away from the droplet interface, thus, leading to a core/shell structure or solid matrix, respectively. Additionally, based on an adaptation of the inventors' reported precision particle fabrication methodology (Berkland 2001, Berkland 2001, Berkland 2002, Berkland 2004) or similar technologies, the inventors can produced a wide range of monodisperse nano clusters (FIG. 4).

A variety of techniques can be used to characterize nano-clusters that have been created by varying nanoparticle type or size, dispersion properties, dispersing materials, and processing conditions. These techniques can be used to mechanistically determine how processing parameters affect particle physicochemical properties. For example, the aerodynamic diameter of a dried nanocluster powder can be determined by an Aerosizer LD (available at the Center for Drug Delivery Research, KU), which will also provide supportive data on dry particle geometric diameter, size distribution, aggregation and density. A helium pycnometer (Micromeritics AccuPyc 1330 helium gas pycnometer) located in Dr. Eric Munson's lab (Pharmaceutical Chemistry, KU) can be used to more accurately determine the density of different nanocluster formulations. For example, a sample of nanocluster powder is measured into a 1 $cm^3$ sample holder and weighed. The density of the sample is determined by helium displacement of the sample compared to a secondary empty chamber. Measurements are conducted in triplicate for each of three samples and the average and standard deviation calculated. Particle exterior and interior morphology (interior viewed via cryo-fracturing (Berkland 2004)) can be investigated via scanning electron microscopy (LEO 1550).

C. Pharmaceutical Compositions and Routes of Administration

One embodiment of this invention includes methods of treating, preventing, or diagnosing a particular disease or condition by administering the disclosed nano-clusters to a subject. In many instances, the nano-clusters are administered alone or can be included within a pharmaceutical composition. An effective amount of a pharmaceutical composition, generally, is defined as that amount sufficient to ameliorate, reduce, minimize or limit the extent of the disease or condition. More rigorous definitions may apply, including elimination, eradication or cure of the disease or condition.

1. Pharmaceutical Compositions

Pharmaceutical compositions of the present invention can include a nano-cluster of the present invention. The phrases "pharmaceutical or pharmacologically acceptable" can include but is not limited to molecular entities and compositions that do not produce an adverse, allergic or other untoward reaction when administered to a subject, such as, for example, a human. The preparation of a pharmaceutical composition is generally known to those of skill in the art. Remington's Pharmaceutical Sciences, 18th Ed. Mack Printing Company, 1990. Moreover, for animal (e.g., human) administration, it is preferred that the preparations meet sterility, pyrogenicity, general safety and purity standards as required by FDA Office of Biological Standards.

"Therapeutically effective amounts" are those amounts effective to produce beneficial results in the recipient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

"Pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990).

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain non-limiting embodiments, pharmaceutical compositions may comprise, for example, at least about 0.1% of an active ingredient or a nano-cluster, for example. In other embodiments, the an active ingredient or nano-cluster may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

The composition may also include various antioxidants to retard oxidation of one or more active ingredient or nano-cluster. The prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The compositions of the present invention may include different types of carriers depending on whether it is to be administered in solid, liquid or aerosol form, and whether it need to be sterile for such routes of administration as injection.

The compositions may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments, the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the compositions are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that exotoxin contamination should be kept minimally at a safe level, for example, less that 0.5 ng/mg protein.

In another aspect of the present invention, a person of ordinary skill will recognize that the compositions of the present invention can include any number of combinations of nano-particles, dispersion materials, active ingredients, and other components. It is also contemplated that that the concentrations of these ingredients can vary. For example, in one-non-limiting aspect, a composition of the present invention can include at least about 0.0001% to about 0.001%, 0.001% to about 0.01%, 0.01% to about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein, of at least one of the nano-particles, dispersion materials, active ingredients, or other components that are mentioned throughout the specification and claims. In non-limiting aspects, the percentage can be calculated by weight or volume of the total composition. A person of ordinary skill in the art would understand that the concentrations can vary depending on the addition, substitution, and/or subtraction of nano-particles, dispersion materials, active ingredients, and other components.

2. Routes of Administration

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrauterinely, intrarectally, intrathecally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990).

D. Combination Therapies

In order to increase the effectiveness of a treatment with the nano-clusters of the present invention, it may be desirable to combine these nano-clusters with other therapies effective in the treatment of a particular disease or condition.

The compositions of the present invention, for example, can precede or follow the other agent treatment by intervals ranging from minutes to weeks. It is contemplated that one may administer both modalities within about 12-24 h of each other and, more preferably, within about 6-12 h of each other. In some situations, it may be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, or more) lapse between the respective administrations.

Various combinations may be employed where a compositions including a nano-cluster is "A" and the secondary agent, is "B":

A/B/A  B/A/B  B/B/A  A/A/B  A/B/B  B/A/A  A/B/B/B

B/A/B/B  B/B/B/A  B/B/A/B  A/A/B/B  A/B/A/B  A/B/B/A

B/B/A/A  B/A/B/A  B/A/A/B  A/A/A/B  B/A/A/A  A/B/A/A

A/A/B/A.

E. Source of Nano-Particles, Dispersion Materials, Active Ingredients, and Other Components The nano-particles, dispersion materials, active ingredients, and other components described in the claims and specification can be obtained by any means known to a person of ordinary skill in the art. In a non-limiting embodiment, for example, these ingredients can be isolated by obtaining the source of such nano-particles, dispersion materials, active ingredients, and other components. Additionally, the ingredients can be purified by any number of techniques known to a person of ordinary skill in the art. Non-limiting examples of purification techniques include Polyacrylamide Gel Electrophoresis, filtration, centrifugation, dialysis, High Performance Liquid Chromatography (HPLC), Gel chromatography or Molecular Sieve Chromatography, and Affinity Chromatography. In other aspects, the compounds, agents, and active ingredients can be obtained by chemical synthesis or by recombinant means by using conventional techniques. See, for example, Stewart and Young, (1984); Tam et al., (1983); Merrifield, (1986); and Barany and Merrifield (1979), Houghten (1985).

F. Kits

In further embodiments of the invention, there is a provided a kit. The kit can include, in non-limiting aspects, the nano-particles, dispersion materials, active ingredients, and other components described in the claims and the specification. In preferred embodiments, the kit can include a composition that includes a nano-cluster. The nano-cluster can include, for example, a plurality of nano-particles and a dispersing material that holds the plurality of nano-particles together and/or disperses the nano-particles in response to an environmental cue.

Containers of the kits can include a bottle, dispenser, package, compartment, or other types of containers, into which a component may be placed. The container can include indicia on its surface. The indicia, for example, can be a word, a phrase, an abbreviation, a picture, or a symbol.

The containers can dispense a pre-determined amount of the component (e.g. compositions of the present invention). The composition can be dispensed in a spray, an aerosol, or in a liquid form or semi-solid form. The containers can have spray, pump, or squeeze mechanisms. In certain aspects, the kit can include a syringe for administering the compositions of the present invention.

Where there is more than one component in the kit (they may be packaged together), the kit also will generally contain a second, third or other additional containers into which the additional components may be separately placed. The kits of the present invention also can include a container housing the components in close confinement for commercial sale. Such containers may include injection or blow-molded plastic containers into which the desired bottles, dispensers, or packages are retained.

A kit can also include instructions for employing the kit components as well the use of any other compositions, compounds, agents, active ingredients, or objects not included in the kit. Instructions may include variations that can be implemented. The instructions can include an explanation of how to apply, use, and maintain the products or compositions, for example.

EXAMPLES

The following examples are included to demonstrate certain non-limiting aspects of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Nano-Clusters with Responsive Dispersion

Nano-Cluster Formation: Nano-clusters of the present invention can be prepared by the following procedure: Two syringe pumps (Harvard Apparatus 4400 and Isco) are connected to the inner and outer ports of a coaxial nozzle to pass a colloidal suspension of nano-particles (see above formulation) in aqueous solution and 1-octanol (Fisher Scientific) as droplet carrying liquid, respectively. The two immiscible liquids are injected at appropriate flows to produce monodisperse aqueous droplets, which contain the colloidal suspension of nano-particles, in the octanol phase. The nano-clusters are formed after water in the droplets dissolves into 1-octanol resulting in packing of the nano-particles into a spherical structure (FIG. 4). Nano-clusters are then washed with ethanol to remove residual 1-octanol and can be freeze dried for analysis. Similar results were achieved by simply adding the nano-particle suspension to the octanol phase and stirring to form a primary emulsion.

Figure 5:
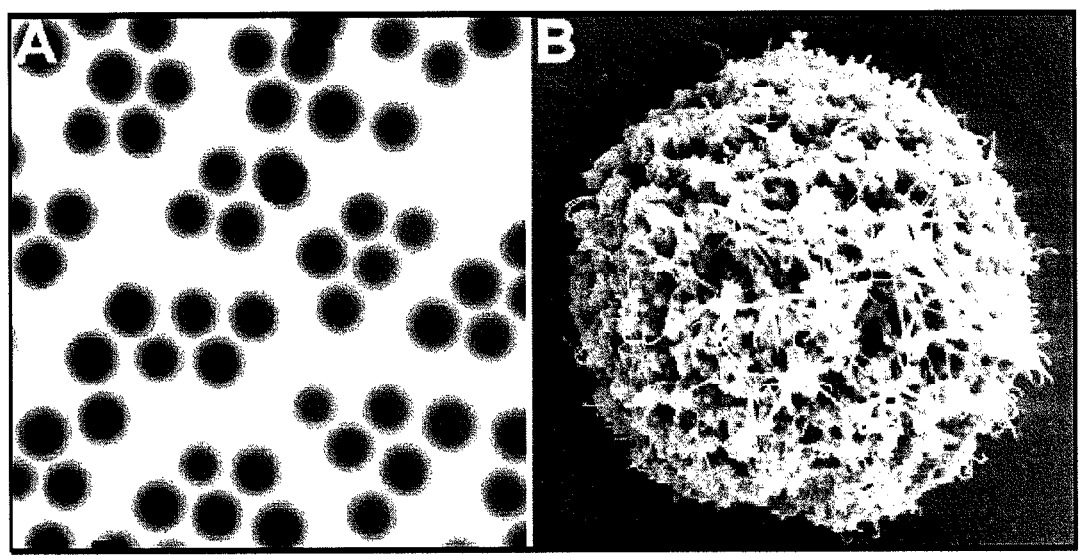

In one non-limiting embodiment, the inventors coated silica nanoparticles with poly(N-vinylformamide) and cross-linked this polymer with a hydrolyzable cross-linker (2-bis [2,2'-di(N-vinylformamido)ethoxy]propane) to form nano-clusters that dispersed in response to a decrease in pH (FIG. 5). This set-up was used to determine the ability to disperse nanoclusters in response to environmental cues.

Figure 6:
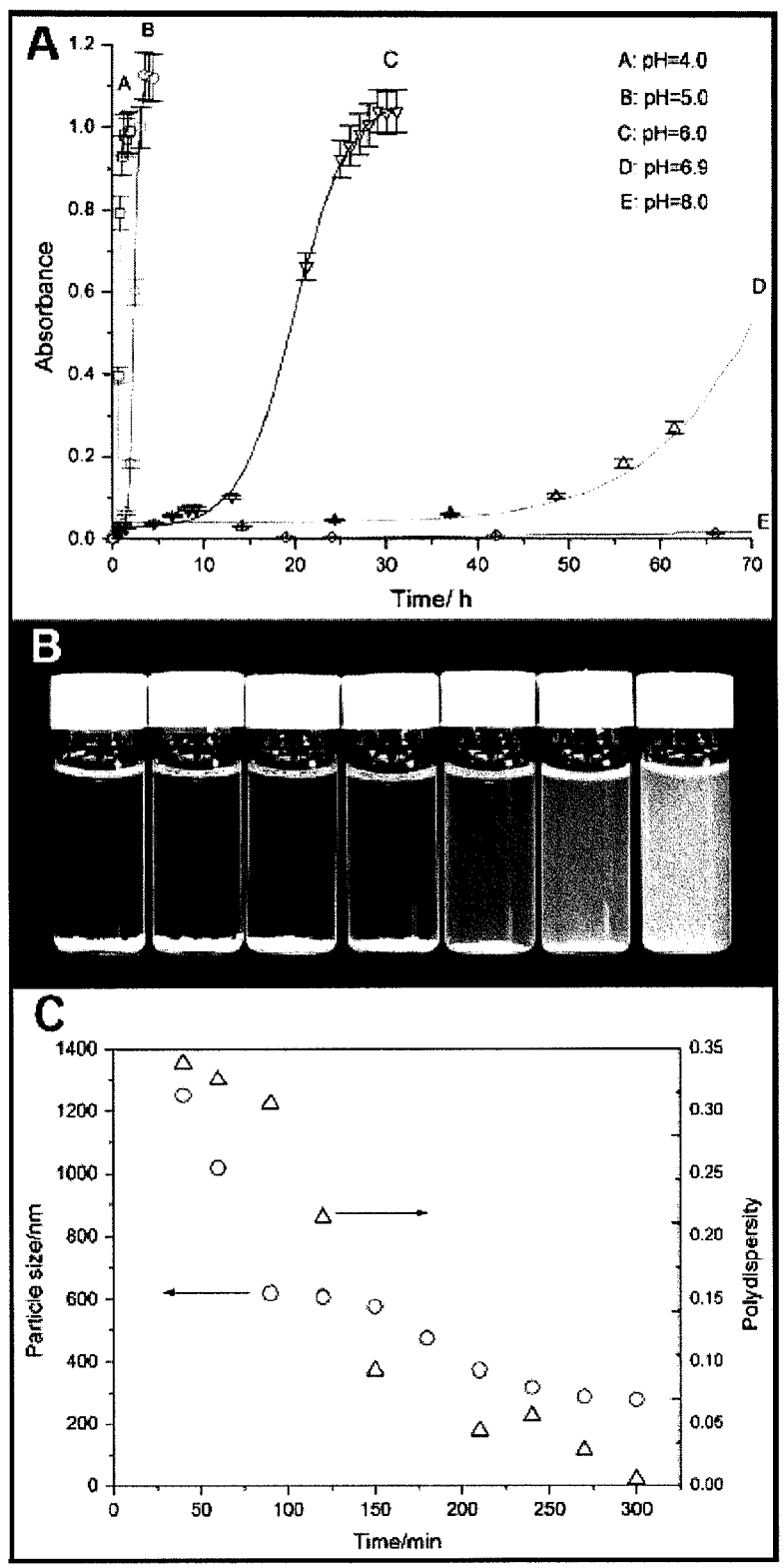

The clustered nanoparticles were slightly different in appearance due to the presence of the polymer, but the size distribution remained consistent with previous experiments. The nanoclusters were dispersed into aqueous solution as a function of time and pH (FIG. 6). A turbidity assay was used to measure optical density at 480 nm over time, the opacity of the solution indicating the relative dispersion of the clusters into constituent nanoparticles. The dispersion of the nano-clusters could also be visually tracked over time (FIG. 6B). Size analysis of the solution phase of dispersed nanoclusters via laser light scattering indicated that polydisperse agglomerates of nanoparticles were liberated. These agglomerates further dispersed into individual nanoparticles over time (FIG. 6C).

Example 2

Self-Assembled Nano-Clusters

Nano-Particle Formation: PLGA nanoparticles were prepared by a modified emulsion/solvent extraction method using different polyelectrolyte coating materials to control surface charge (Table 1). Polyvinylamine (PV Am) was used as a cationic coating material and was synthesized in house (see Experimental). Polyethylene-alt-maleic acid (PEMA) was synthesized by hydrolysis of the anhydride from of this polymer as adapted from methods reported previously. The resulting polyelectrolyte-coated PLGA nanoparticles possessed excellent uniformity and high surface charge (Table 1). Each nano-particle formulation was analyzed for size and zeta potential using dynamic light scattering and conductivity measurements (Brookhaven ZetaPALS), respectively, in the appropriate media (water or organic). Studies confirmed the maintenance of particle surface charge upon lyophilization and after more than one week of incubation at 37° C., pH 7.4 (data not shown). PVAm-coated nanoparticles were notably larger than PEMA-coated nanoparticles for this experiment; however, this size is readily controlled. Nano-particles can be made by using reported techniques, for example; emulsion polymerization, emulsion solvent extraction, reverse emulsions of the same, precipitation, crystallization, freeze drying, spray freeze drying, salting out, etc. (Wittaya-Areekul et al. 2002).

TABLE 1

(PLGA nanoparticle properties)

| PLGA Nanoparticle | Size (nm) | Zeta potential (mV) |
|---|---|---|
| PVAm-coated | 498.5 ± 8.4 | +30.7 ± 1.0 |
| PEMA-coated | 262.7 ± 11.3 | −52.3 ± 1.2 |

Figure 7:
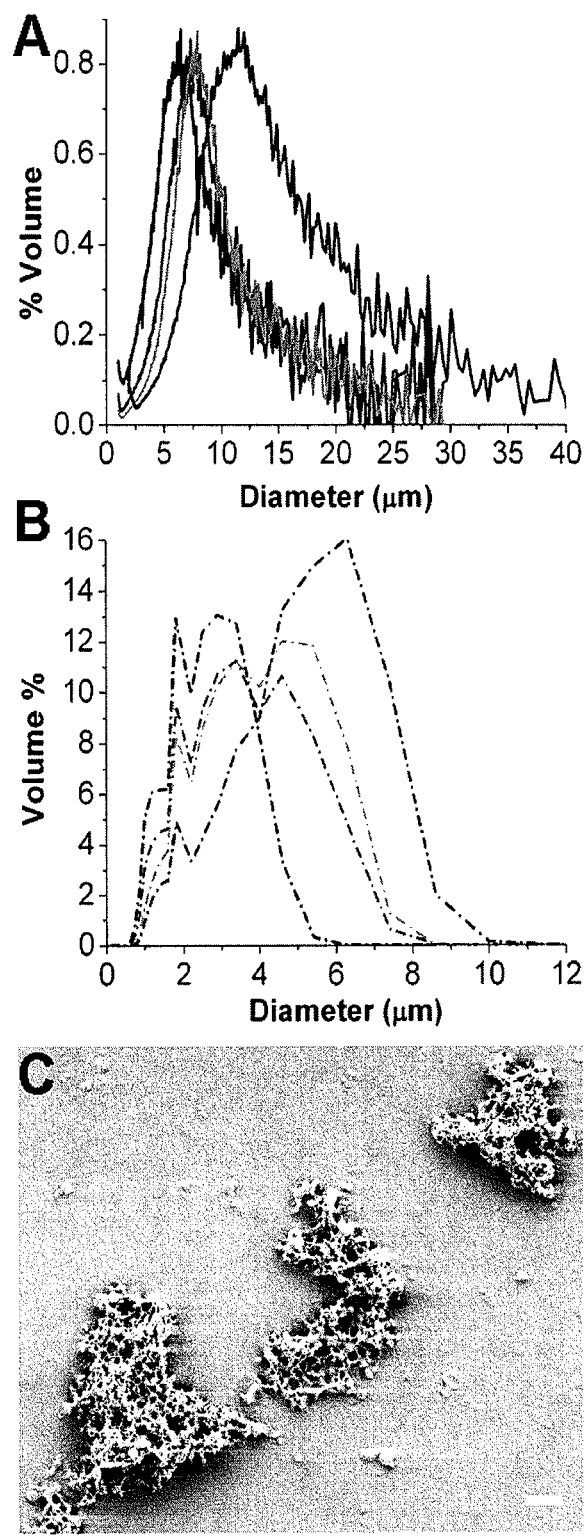
Figure 8:
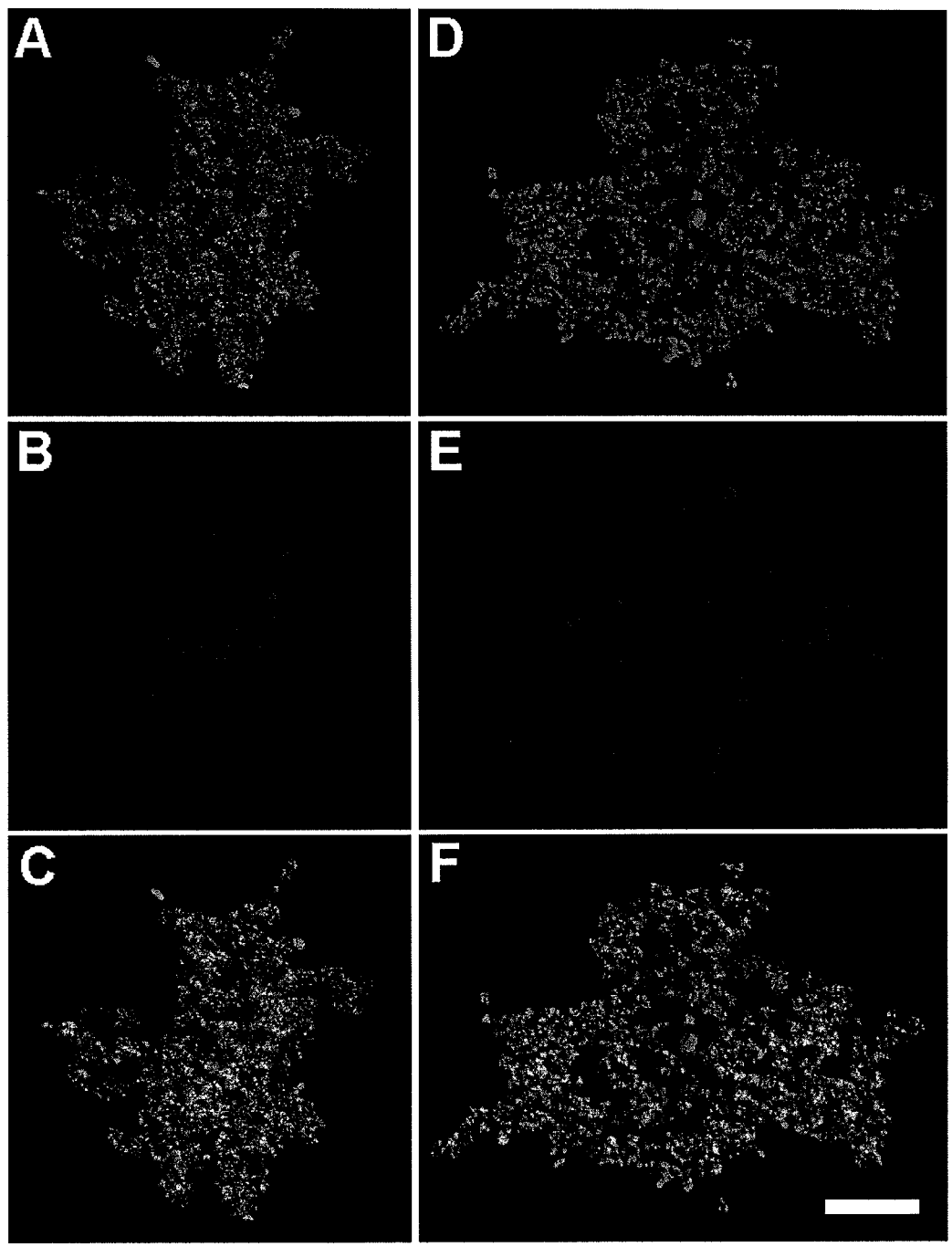

Nano-Cluster Formation: Nanoparticle clusters were produced by slow addition of 3 mL of PVAm-coated nanoparticles into 10 mL of PEMA-coated nanoparticles under gentle stirring. Nano-cluster formation was induced by electrostatic self-assembly of the oppositely charged nanoparticles. Increasing the concentration of mixed nanoparticles resulted in a corresponding increase in the cluster diameter (FIG. 7). The geometric size distribution of nanoclusters was determined in aqueous solution (Isoton) using a Coulter Multisizer III. Geometric size distributions were relatively broad exhibiting standard deviations that were 60-70% of the average geometric diameter. The aerodynamic size distributions were determined from freeze dried nanoclusters using time of flight measurements obtained by an Aerosizer LD. Nanocluster aerodynamic size distributions were narrower than the geometric size distributions as indicated by the increased volume percent (FIG. 7B) and decreased standard deviations (35-60% of the mean; Table 2). Free PEMA-coated nanoparticles were detected as a rising tail in the geometric size distributions, but were not detected in the aerodynamic size distributions. In addition, few free nanoparticles were observed in scanning electron micrographs (FIG. 7C) indicating that nanoparticles that were not associated with nanoclusters in solution bound to nanoclusters during lyophilization.

TABLE 2

(Dependence of the size of nanocluster on the concentration of PLGA nanoparticles)

| | PLGA NP conc. (mg/ml) | | | |
|---|---|---|---|---|
| | (−)* 0.68 (+)** 0.72 | (−) 1.36 (+) 1.44 | (−) 2.04 (+) 2.16 | (−) 2.72 (+) 2.82 |
| $d_{geo}$ (μm) | 7.4 ± 5.1 | 8.7 ± 5.6 | 9.4 ± 5.6 | 13.7 ± 8.3 |
| $d_{aero}$ (μm) | 2.4 ± 1.5 | 3.0 ± 1.6 | 3.4 ± 1.6 | 4.4 ± 1.6 |
| $d_{geo}/d_{aero}$ | 0.33 ± 0.29 | 0.35 ± 0.29 | 0.36 ± 0.29 | 0.32 ± 0.19 |
| Calculated ρ[1] ($g/cm^3$) | 0.11 ± 0.09 | 0.12 ± 0.08 | 0.13 ± 0.08 | 0.10 ± 0.04 |
| Fine Particle Fraction[2] | 1.00 | 0.80 | 0.75 | 0.50 |

*(−): PLGA nanoparticles with negative surface charge (PEMA-coated)
**(+): PLGA nanoparticles with positive surface charge (PVAm-coated)
[1]Density calculated from Equation 1 using $d_{geo} = d_p$, $\rho_{ref} = 1\ g/cm^3$ and $\gamma = 1$.
[2]Fine Particle Fraction defined as the fraction of dry particles with $d_{aero} < 5$ μm.

Structural analysis of nanoclusters revealed a low density, web-like morphology. Scanning electron micrographs showed that freeze dried nanoparticle clusters possessed a large amount of porosity (FIG. 7C). The density of each nanocluster formulation was calculated from the geometric and aerodynamic diameters according to equation 1 (Table 2). Although nanocluster size increased with increasing nanoparticle concentration, the calculated density was essentially the same for each. The calculated densities of nanoclusters were quite low (~0.15 $g/cm^3$) and yielded a very high fine particle fraction ($d_{aero}$<5 μm) for most formulations. The use of a hydrated geometric diameter, dehydrated aerodynamic diameter, and the assumed shape factor of γ=1 (i.e. a sphere) should be noted when interpreting this density calculation.

Laser scanning cofocal microscopy was utilized to gain more insight into the nanocluster structure and formation mechanism. PVAm-coated nanoparticles were labeled with a green fluoroisothiocyanate (FITC) dye and PEMA-coated nanoparticles were labeled with a red rhodamine dye. Detailed analysis of two nanocluster particles indicated that both PVAm-coated (FIG. 8A and FIG. 8D) and PEMA-coated (FIG. 8B and FIG. 8E) nanoparticles were present throughout the entire nanocluster structure.

Example 3

Preparation of Nifedipine and Loratadine Nanoparticles

The following includes examples of preparing various non-limiting nifedipine and loratadine nanoparticles.

1020 nm Nifedipine nanoparticle—Nifedipine (50 mg) was dissolved in 3 ml of methylene chloride. Dumped nifedipine solution into 0.125% Cetyltrimethylammonium bromide (CTAB) solution (30 mL) and sonicated for 60 s. The particle suspension was placed into a hood for two hours to evaporate the methylene chloride. The resulting nanoparticle had a particle size of 1020 nm and a polydispersity of 0.24.

660 nm Nifedipine nanoparticle—Nifedipine (50 mg) was dissolved in 3 ml of methylene chloride. Dumped nifedipine solution into 0.5% CTAB solution (30 mL) and sonicated for 60 s. The particle suspension was placed into a hood for two hours to evaporate the methylene chloride. The resulting nanoparticle had a particle size of 660 nm and a polydispersity of 0.17.

480 nm Nifedipine nanoparticle—Nifedipine (50.2 mg) was dissolved in 3 ml of ethanol. Dumped nifedipine solution into 0.5% CTAB solution (30 mL) and sonicated for 60 s. The particle suspension was placed into a hood for two hours to evaporate the ethanol. The resulting nanoparticle had a particle size of 480 nm and a polydispersity of 0.12.

2373 nm Nifedipine nanoparticle—Nifedipine (30 mg) was dissolved in 2 ml of ethanol. Dumped nifedipine solution into 0.3% Pluronic F-68 solution (30 mL) and homogenized at 15,000 rpm for 60 s. The particle suspension was placed into a hood for two hours to evaporate the ethanol. The resulting nanoparticle had a particle size of 2373 nm and a polydispersity of 0.09.

897 nm Nifedipine nanoparticle—Nifedipine (30 mg) was dissolved in 2 ml of ethanol. Dumped nifedipine solution into 0.6% Pluronic F-68 solution (30 mL) and homogenized at 15,000 rpm for 60 s. The particle suspension was placed into a hood for two hours to evaporate the ethanol. The resulting nanoparticle had a particle size of 897 nm and a polydispersity: 0.07.

639 nm Nifedipine nanoparticle—Nifedipine (30 mg) was dissolved in 2 ml of ethanol. Dumped nifedipine solution into 0.9% Pluronic F-68 solution (30 mL) and homogenized at 15,000 rpm for 60 s. The particle suspension was placed into a hood for two hours to evaporate the ethanol. Resulting nanoparticle had a particle size of 639 nm and a polydispersity of 0.005.

391 nm Loratadine nanoparticle—Loratadine (10 mg) was dissolved in 1 ml of ethanol. Dumped loratadine solution into 0.9% Pluronic F-68 solution (10 mL) and homogenized at 15,000 rpm for 60 s. The particle suspension was placed into a hood for two hours to evaporate the ethanol. The resulting nanoparticle had a particle size of 391 nm and a polydispersity of 0.005.

Example 4

Preparation of Nifedipine Nanoparticle Clusters

This example provides a non-limiting embodiment of the present invention where the nanoparticle is pure nifedipine (a calcium channel blocker that treats high blood pressure). The nanoparticle is coated with a cationic surfactant (CTAB). A polyanion (sodium alginate) couples with the CTAB which induces nanocluster formation.

Figure 9:
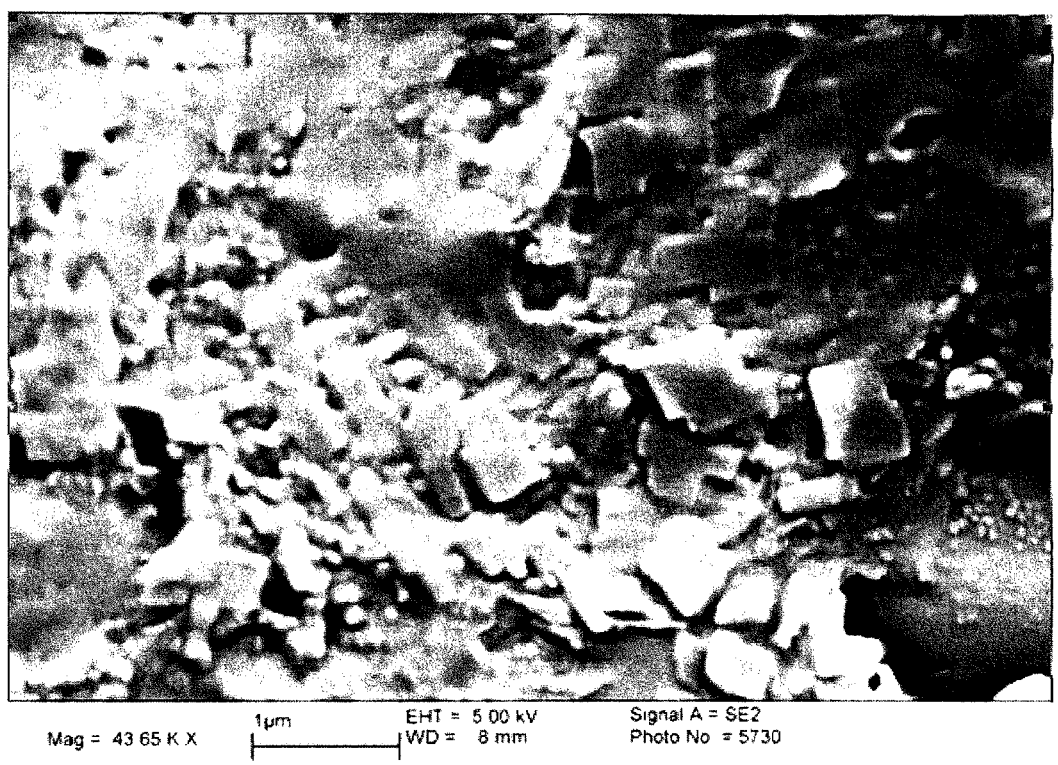

Preparation of nifedipine nanoparticles: Nifedipine (50 mg) was dissolved in methylene chloride (3 ml). The solution was poured completely into a CTAB concentration-known aqueous solution (Table 3). The solution was sonicated for 60 s. Subsequently, the particle suspension was placed into a hood for two hours to evaporate the methylene chloride. The suspension was diluted to 1 mg/ml. FIG. 9 is a scanning electron microscope (SEM) image of a population of nifedipine nanoparticles.

TABLE 3

(Geometric size and aerodynamic diameters of clusters*)

| Conc. of CTAB (wt %) | $V_{Nifedipine}/V_{algenic\ acid}$ | Geometric size (µm) | Dynamic diameter (before grinding) (µm) | Dynamic diameter (after grinding) (µm) |
|---|---|---|---|---|
| 0.125 | 2:1 | 28.11 ± 8.33 | 3.313 ± 1.868 | 3.321 ± 1.763 |
| | 1:1 | 22.84 ± 11.64 | 3.814 ± 1.811 | 4.133 ± 1.829 |
| | 1:2 | 29.27 ± 11.47 | 4.219 ± 1.597 | 4.234 ± 1.836 |
| | 1:3 | 23.31 ± 13.4 | 3.397 ± 1.858 | 3.702 ± 1.844 |
| 0.25 | 2:1 | 27.24 ± 11.42 | 3.775 ± 1.804 | 3.467 ± 2.025 |
| | 1:1 | 29.49 ± 12.36 | 3.98 ± 1.868 | 4.135 ± 1.803 |
| | 1:2 | 23.36 ± 13.48 | 4.217 ± 1.874 | 4.312 ± 1.926 |
| | 1:3 | 23.82 ± 10.50 | 3.520 ± 1.989 | 4.006 ± 1.903 |
| 0.4 | 2:1 | 26.39 ± 12.76 | 3.819 ± 1.786 | 4.715 ± 1.397 |
| | 1:1 | 33.74 ± 13.85 | 4.156 ± 1.769 | 3.840 ± 1.942 |
| | 1:2 | 30.97 ± 14.31 | 3.793 ± 1.866 | 3.973 ± 1.876 |
| | 1:3 | 23.72 ± 15.70 | / | / |

*Concentration: particle suspension: 1 mg/ml; Algenic acid: 1 mg/ml

Figure 10:
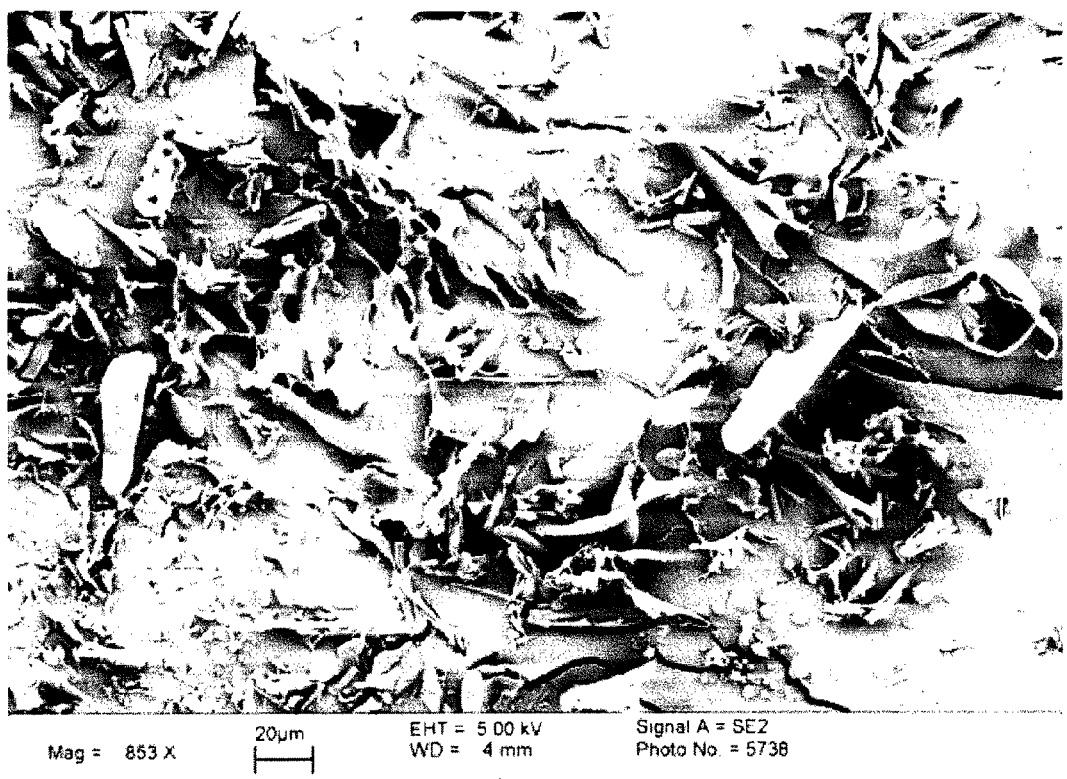

Preparation of nifedipine nanoparticle clusters: Algenic acid aqueous solution (10 ml, 1 mg/ml) was poured into nifedipine nanoparticle aqueous suspension (10 ml, 1 mg/ml) and the mixture was homogenized with a homogenizer (about 2000 rpm) for 2 min. Dry Nifedipine nanoparticle clusters were obtained by freeze-drying. FIG. 10 is a SEM image of nifedipine nanoparticle clusters.

Example 5

Nanocluster Comprising Ovalbumin

This example provides a non-limiting embodiment of the present invention where the nanoparticle is a biodegradable polymer (PLGA) coated with a cationic lipid (DOTAP). Ovalbumin couples to the surface of the coated nanoparticle which induces nanocluster formation.

Preparation of nanoparticles: PLGA nanoparticles were prepared using a modified emulsion-solvent evaporation technique (Kazzaz et al., 2000; Mainardes et al., 2005, both of which are incorporated by reference). A cationic surface charge was incorporated using the lipid 1,2-dioleoyl-3-trimethylammonium-propane (DOTAP; Avanti Polar Lipids, Inc.; Alabaster, Ala.) as the coating material. 3 mL PLGA (0.41 dL/g inherent viscosity; Lactel; Pelham, Ala.) dissolved in an acetone/methanol mixture (5/1) at 1.67% (w/v) was added to 25 mL DOTAP (50 µM) and sonicated at 50% power using a sonic dismembrator (Fisher Scientific; Pittsburgh, Pa.) for 60 s on ice. This was repeated for a total of 6 batches. The batches were combined and stirred at moderate speed in the hood overnight to evaporate the solvent. The particles were crudely filtered through a KimWipe and washed three times with ~15 mL distilled, deionized water using an Amicon Ultra-15 centrifugal filter unit (Millipore; Billerica, Massachusetts; F=863 g). The washed nanoparticles were sonicated in a water bath for 15 min and again filtered through a KimWipe to remove any large agglomerates. The resulting particles were then characterized using a Zeta Potential Analyzer (Brookhaven Instruments; Holtsville, N.Y.) to measure particle size and surface charge ($\zeta$): the nanoparticles had an average size of 343.0±8.6 (nm), a polydispersity of 0.232±0.022, and a zeta potential of 36.44±0.56 (mV). The nanoparticle suspension was diluted in 1 mM sodium nitrate solution for surface charge measurements.

Figure 11:
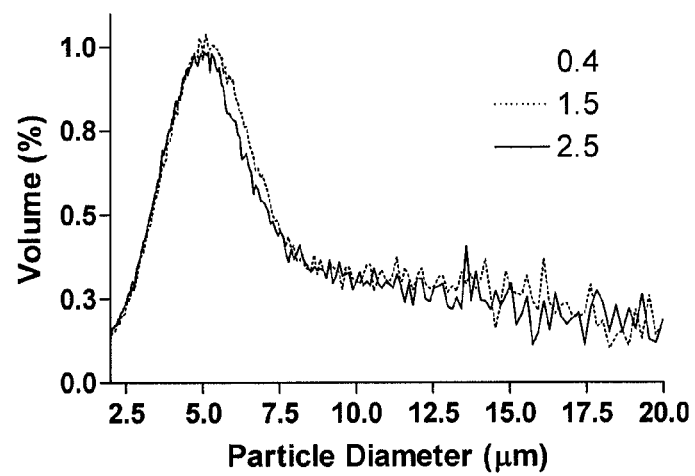

Spontaneous nanocluster formation of nanoparticles with ovalbumin: Ovalbumin was used as a model protein. Three solutions containing approximately 0.4, 1.5 and 2.5 mg/mL ovalbumin were prepared in phosphate buffered saline (PBS), and the exact concentration of each solution was determined using UV absorbance spectroscopy (Table 4). Three labeled, 15 mL centrifuge tubes, 6 mL DOTAP nanoparticles and 1 mL ovalbumin solution were added. The samples were tumbled gently on an end-over-end tube rotator for 45 min at 4° C. The resulting nanoclusters were analyzed using a Multisizer 3 Coulter Counter (Beckman Coulter, Inc.; Fullerton, Calif.) to measure their geometric diameter. The nanoclusters were lyophilized using a Labconco bench-top lyophilizer (Kansas City, Mo.) and further characterized to determine the aerodynamic diameter (Aerosizer; Amherst Process Instruments Inc.) and morphology (SEM) (Table 5). FIG. 11 illustrates the geometric diameter of the DOTAP/PLGA nanoparticles with ovalbumin.

TABLE 4

(Concentration of ovalbumin solutions as determined by UV absorbance spectroscopy)

| Target Concentration (mg/mL) | Actual Concentration (mg/mL) |
|---|---|
| 0.4 | 0.371 ± 0.001 |
| 1.5 | 1.374 ± 0.003 |
| 2.5 | 2.236 ± 0.040 |

TABLE 5

(Nanocluster sizes)

| Target concentration of ovalbumin (mg/mL) | Mode Geometric Diameter* (μm) | Mean Aerodynamic Diameter (μm) |
|---|---|---|
| 0.4 | 6.25 | 2.384 ± 1.775 |
| 1.5 | 5.15 | 2.468 ± 1.931 |
| 2.5 | 5.10 | 2.447 ± 1.918 |

*See FIG. 11 for size distribution.

Figure 12:
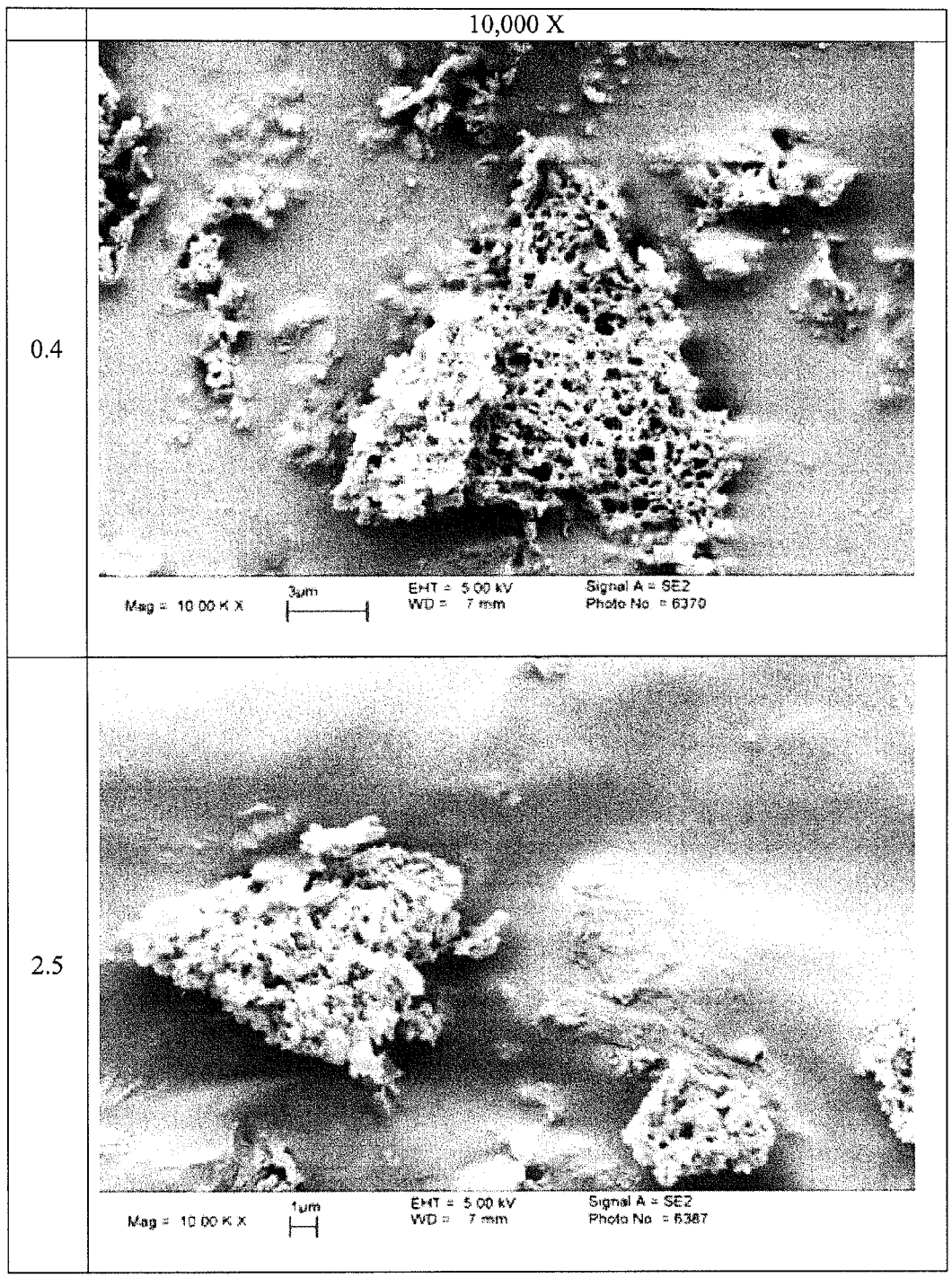

Scanning electron microscopy (SEM): The size and morphology of the nanoclusters were evaluated using a LEO 1550 field emission scanning electron microscope with secondary electron detection. The nanoclusters were coated on a platform and sputtered with gold prior to imaging at 4000 and 10,000×0 magnification. FIG. 12 includes SEM images of the nanoclusters comprising DOTAP/PLGA nanoparticles and ovalbumin.

Example 6

Assessment of Dry Powder Performance In Vitro

A multi-stage liquid impactor (MSLI) fitted with a mouthpiece and throat assembly (el-Araud et al. 1998) can be used to evaluate the deposition performance of various particle formulations administered from a dry powder inhaler. For administraton through a dry powder inhaler (DPI) such as the Spinhaler(® or Rotahaler®, particles are first encapsulated in a large, two-piece gelatin capsule. The capsule is placed into a small compartment in the DPI, which is then twisted to either separate or rupture the capsule immediately prior to breath actuation. Since no propelants or compressed gases are used for these DPIs, the breathing force of the patient, or in our case the volumetric flow rate through the MSLI, disperses the powder.

Using this experimental set-up, several important performance parameters can be evaluated, including the respirable fraction of a particle formulation, the mass depositing in the mouthpiece and throat assembly and the fractions of particles depositing at different stages throughout the MSLI (assesed by removing each section and weighing the collected particle mass). Particle batches depositing with high efficiency to the lower stages (~1-5 μm cut-off) of the MSLI will be deemed as "deep lung" formulations suitable for ciprofloxacin encapsulation experiments.

Example 7

Identification of Nano-Cluster Formulations that Can Entrap, Deposit, and Release Ciprofloxacin Nano-clusters can be formulated for controlled release of ciprofloxacin for ~1 week. A complete analysis of nanocluster physicochemical properties, dispersion and release of the drug can be prepared by the methods described throughout this specification. The nano-clusters, in one embodiment, can be made with nano-particles of pure ciprofloxacin or ciprofloxacin encapsulated in PLGA nano-particles.

Ciprofloxacin is a broad spectrum antibiotic, especially effective against gram negative bacteria (Geller 2002, Geller 2003, Marier 2003) having the following formula:

Nano-cluster dispersability and ciprofloxacin release kinetics: Nanocluster formulations can be reformulated to determine controlled release of ciprofloxacin, taking care to maintain the same fabrication procedure and resulting structure designed for deep lung deposition. Ciprofloxacin (Sigma, Inc.) can be encapsulated by co-dissolving with the polymer phase and will be partially suspended in the polymer phase or dissolved in a co-solvent if low solubility in the polymer phase is an issue. Dissolution studies ascertain the release kinetics of ciprofloxacin. These studies are performed in phosphate buffered saline solution (pH 7.4) at physiological temperature (37° C.). Approximately 10-20 mg of each particle formulation is placed in 2 mL microcentrifuge tubes shaken at 150 rpm. Release samples will be tested by intermittently centrifuging samples to separate nanoparticles (15, 000 rpm), collecting 1-1.5 mL of supernatant, replacing supernatant with fresh buffer and resuspending the samples. The supernatant will then be analyzed by spectrophotometry at ~350 nm to determine the concentration of ciprofloxacin at each time point while avoiding detection of polymer dissolution products. The release of ciprofloxacin from the various nanocluster formulations will be conducted in triplicate and the average and standard deviation is calculated. The initial loading of ciprofloxacin in nanocluster formulations is determined by dissolving ~10 mg of each formulation in triplicate in dimethylsulfoxide and measuring the absorbance at ~350 nm. Absorbance values for formulations of nanoclusters without ciprofloxacin are used as blanks. The calculated amount of ciprofloxacin per mass of polymer is termed the drug loading. This number can be divided by the mass of ciprofloxacin per mass of polymer entered into the experiment to calculate the drug encapsulation efficiency. The summed mass of ciprofloxacin released over time is then divided by the drug loading to arrive at the cumulative percent released. Analogous samples of nanoclusters can be prepared to determine the dispersion kinetics based on measuring the turbidity of the sample solution at 480 nm (see preliminary data above).

Reformulation and optimization of controlled release: Generating a near constant release of ciprofloxacin for ~1 week may include reformulation of nanoclusters. If drug "bursting" (rapid initial release) occurs or increased duration of release is desired, higher molecular weight PLGA or PLGA with a higher lactide content will be used as each of these prolong degradation of the polymer phase. In addition, increasing the size of constituent nano-particles to decrease the rate of ciprofloxacin release can be used. The maintenance of small (e.g., <200 nm) nano-particles can be used as a way to avoid phagocytosis or other clearance mechanisms from the lung epithelium.

All of the compositions and/or methods disclosed and claimed in this specification can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Publication 2003/0138490

Adjei and Garren, *Pharm. Res.*, 7(6):565-569, 1990.

AHFS 99 Drug Information

Amer. Soc. of Health System, ISBN: 1879907917

Barany and Merrifield, In: *The Peptides*, Gross and Meienhofer (Eds.), Academic Press, NY, 1-284, 1979.

Berkland et al., In: *Precision polymer microparticles for controlled-release drug delivery*, ACS Symp Ser., 2002.

Berkland et al., *J. Control Release,* 73(1):59-74, 2001.

Berkland et al., *J. Control Release,* 82(1):137-47, 2002.

Berkland et al., *J. Control Release,* 96(1):101-111, 2004.

Berkland, In: *Methods of controlling size distribution of polymeric drug delivery particles*, Chemical Engineering, Urbana-Champaign, University of Illinois, 78, 2001.

Edwards et al., *J. Appl. Physiol.,* 85(2):379-385, 1998.

Edwards etal., *Science,* 276:1868-1887, 1997.

El-Araud et al., *J Pharm Pharmacol,* 50(10):1081-5, 1998.

Geller et al., *Chest,* 122(1):219-226, 2002.

Geller et al., *Chest,* 123(1):28-36, 2003.

Grenha et al., *Eur. J. Pharm. Sci.,* 25(4-5):427-437, 2005.

Griesenbach et al., *Curr. Opin. Pulm. Med.,* 10(6):542-546, 2004.

Houghten et al., *Infect. Immun.,* 48(3):735-740., 1985.

John et al., *Faseb. J.,* 17(15):2296-2298, 2003.

Johnson et al., *Chest,* 96(1):6-10, 1989.

Kazzaz et al., *J Control Release,* 67:347-56, 2000.

Kumar et al., *Genet. Vaccines Ther.,* 1(1):3, 2003.

Mainardes et al., *J Microencapsul,* 22:13-24, 2005.

Marier et al., *J. Antimicrob. Chemother.,* 52(2):247-252, 2003.

Merrifield, *Science,* 232(4748):341-347, 1986.

Newman et al., *Eur. Respir. J.,* 16(1):178-183, 2000.

Newman, *Curr. Opin. Pulm. Med.,* 9(1):S17-20, 2003.

Physician's Desk Reference. $54^{th}$ Ed., 2000

Rasenack and Muller, *Pharm. Dev. Technol.,* 9(1):1-13, 2004.

Remington's Pharmaceutical Sciences, 18th Ed. Mack Printing Company, 1289-1329, 1990.

Sham et al., *Int. J. Pharm.,* 269(2):457-467, 2004.

Stewart and Young, In: *Solid Phase Peptide Synthesis,* 2d. ed., Pierce Chemical Co., 1984.

Tam et al., *J. Am. Chem. Soc.,* 105:6442, 1983.

Wittaya-Areekul et al., *J. Pharm. Sci.,* 91(4):1147-1155, 2002.

The invention claimed is:

1. A nano-cluster comprising a plurality of nano-particles, wherein the nano-particles include an active ingredient and a polymer, and wherein the nano-cluster is not hollow.

2. The nano-cluster of claim 1, wherein the active ingredient is bound to the surface of the nano-particles.

3. The nano-cluster of claim 1, wherein the size of the nano-cluster is from about 1 to about 200 microns.

4. The nano-cluster of claim 1, wherein the nano-cluster is solid.

5. The nano-cluster of claim 1, wherein the nano-particles are not covalently bonded together.

6. The nano-cluster of claim 1, wherein the nano-particles are not encapsulated.

7. The nano-cluster of claim 1, wherein the nano-particles disperse in response to an environmental cue.

8. The nano-cluster of claim 1, wherein the nano-particle is solid.

9. The nano-cluster of claim 1, wherein the nano-particle is hollow.

10. The nano-cluster of claim 1, further comprising a dispersing material that disperses the nano-particles in response to an environmental cue.

11. The nano-cluster of claim 10, wherein the dispersing material comprises a water soluble polymer, a biodegradable polymer, a polyelectrolyte, a metal, a polymeric cross-linker, a small molecule cross-linker, a pH sensitive material, a surfactant, or a temperature sensitive material.

12. The nano-cluster of claim 10, wherein the environmental cue is water, a selected pH, a selected temperature, the presence of a selected enzyme, the presence of a selected chemical, the presence of a selected electromagnetic wavelength range, or the presence of vibration or shearing.

13. The nano-cluster of claim 1, comprising at least 50% by weight of nano-particles.

14. The nano-cluster of claim 1, wherein the nano-cluster is comprised in a composition.

15. The nano-cluster of claim 14, wherein the composition further comprises an active ingredient.

16. The nano-cluster of claim 14, wherein the composition is formulated into a dry powder, an aerosol, a spray, a tablet, or a liquid.

17. The nano-cluster of claim 14, wherein the composition is formulated into a pharmaceutically acceptable carrier.

18. A nano-cluster comprising a plurality of nano-particles, wherein the nano-particles include an active ingredient and a biodegradable polymer, and wherein the nano-cluster is not hollow.

19. The nano-cluster of claim 18, wherein the active ingredient is bound to the surface of the nano-particles.

20. The nano-cluster of claim 18, wherein the size of the nano-cluster is from about 1 to about 200 microns.

21. The nano-cluster of claim 18, wherein the nano-cluster is solid.

22. The nano-cluster of claim 18, wherein the nano-particles are not covalently bonded together.

23. The nano-cluster of claim 18, wherein the nano-particles are not encapsulated.

24. The nano-cluster of claim 18, wherein the nano-particles disperse in response to an environmental cue.

25. The nano-cluster of claim 18, wherein the nano-particle is solid.

26. The nano-cluster of claim 18, wherein the nano-particle is hollow.

27. The nano-cluster of claim 18, further comprising a dispersing material that disperses the nano-particles in response to an environmental cue.

28. The nano-cluster of claim 27, wherein the dispersing material comprises a water soluble polymer, a biodegradable polymer, a polyelectrolyte, a metal, a polymeric cross-linker, a small molecule cross-linker, a pH sensitive material, a surfactant, or a temperature sensitive material.

29. The nano-cluster of claim 27, wherein the environmental cue is water, a selected pH, a selected temperature, the presence of a selected enzyme, the presence of a selected chemical, the presence of a selected electromagnetic wavelength range, or the presence of vibration or shearing.

30. The nano-cluster of claim 18, comprising at least 50% by weight of nano-particles.

31. The nano-cluster of claim 18, wherein the nano-cluster is comprised in a composition.

32. The nano-cluster of claim 31, wherein the composition further comprises an active ingredient.

33. The nano-cluster of claim 31, wherein the composition is formulated into a dry powder, an aerosol, a spray, a tablet, or a liquid.

34. The nano-cluster of claim 31, wherein the composition is formulated into a pharmaceutically acceptable carrier.

35. A nano-cluster comprising a plurality of nano-particles, wherein the nano-particles include an active ingredient, and wherein the nano-cluster is not hollow and is comprised in a composition formulated into a dry powder, an aerosol, a spray, a tablet, or a liquid.

36. The nano-cluster of claim 35, wherein the active ingredient is bound to the surface of the nano-particles.

37. The nano-cluster of claim 35, wherein the size of the nano-cluster is from about 1 to about 200 microns.

38. The nano-cluster of claim 35, wherein the nano-cluster is solid.

39. The nano-cluster of claim 35, wherein the nano-particles are not covalently bonded together.

40. The nano-cluster of claim 35, wherein the nano-particles are not encapsulated.

41. The nano-cluster of claim 35, wherein the nano-particles disperse in response to an environmental cue.

42. The nano-cluster of claim 35, wherein the nano-particle is solid.

43. The nano-cluster of claim 35, wherein the nano-particle is hollow.

44. The nano-cluster of claim 35, further comprising a dispersing material that disperses the nano-particles in response to an environmental cue.

45. The nano-cluster of claim 44, wherein the dispersing material comprises a water soluble polymer, a biodegradable polymer, a polyelectrolyte, a metal, a polymeric cross-linker, a small molecule cross-linker, a pH sensitive material, a surfactant, or a temperature sensitive material.

46. The nab-cluster of claim 44, wherein the environmental cue is water, a selected pH, a selected temperature, the presence of a selected enzyme, the presence of a selected chemical, the presence of a selected electromagnetic wavelength range, or the presence of vibration or shearing.

47. The nano-cluster of claim 35, comprising at least 50% by weight of nano-particles.

48. The nano-cluster of claim 35, wherein the composition further comprises an active ingredient.

49. A nano-cluster comprising a plurality of nano-particles, wherein the nano-particles include an active ingredient, and wherein the nano-cluster is not hollow and is comprised in a composition formulated into a pharmaceutically acceptable carrier.

50. The nano-cluster of claim 49, wherein the active ingredient is bound to the surface of the nano-particles.

51. The nano-cluster of claim 49, wherein the size of the nano-cluster is from about 1 to about 200 microns.

52. The nano-cluster of claim 49, wherein the nano-cluster is solid.

53. The nano-cluster of claim 49, wherein the nano-particles are not covalently bonded together.

54. The nano-cluster of claim 49, wherein the nano-particles are not encapsulated.

55. The nano-cluster of claim 49, wherein the nano-particles disperse in response to an environmental cue.

56. The nano-cluster of claim 49, wherein the nano-particle is solid.

57. The nano-cluster of claim 49, wherein the nano-particle is hollow.

58. The nano-cluster of claim 49, further comprising a dispersing material that disperses the nano-particles in response to an environmental cue.

59. The nano-cluster of claim 58, wherein the dispersing material comprises a water soluble polymer, a biodegradable polymer, a polyelectrolyte, a metal, a polymeric cross-linker, a small molecule cross-linker, a pH sensitive material, a surfactant, or a temperature sensitive material.

60. The nano-cluster of claim 58, wherein the environmental cue is water, a selected pH, a selected temperature, the presence of a selected enzyme, the presence of a selected chemical, the presence of a selected electromagnetic wavelength range, or the presence of vibration or shearing.

61. The nano-cluster of claim 49, comprising at least 50% by weight of nano-particles.

62. The nano-cluster of claim 49, wherein the composition further comprises an active ingredient.

* * * * *

UNITED STATES PATENT AND TRADEMARK OFFICE
CERTIFICATE OF CORRECTION

PATENT NO. : 7,651,770 B2
APPLICATION NO. : 11/610986
DATED : January 26, 2010
INVENTOR(S) : Cory J. Berkland and Lianjun Shi It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 254 days.

Column 1, line 31
After "delivered by"", insert --polycationic-- and delete "polycantionic".

Column 2, line 35
Before "hydroxyl,", insert --sulfhydryl,-- and delete "sulhydryl".

Column 10, line 2
Before "hydroxyl,", insert --sulfhydryl,-- and delete "sulhydryl".

Column 10, line 25
After "polyoxyethylene", insert --derivatives-- and delete "deriviatives".

Signed and Sealed this

Twentieth Day of July, 2010

David J. Kappos
*Director of the United States Patent and Trademark Office*